United States Patent
Gerwert et al.

(10) Patent No.: US 12,031,907 B2
(45) Date of Patent: Jul. 9, 2024

(54) ATTENUATED TOTAL REFLECTANCE-BASED BIOSENSOR FOR CONFORMATION AND SECONDARY STRUCTURE ANALYSIS

(71) Applicant: betaSENSE GmbH, Münster (DE)

(72) Inventors: Klaus Gerwert, Münster (DE); Jens Wiltfang, Essen (DE); Julian Ollesch, Witten (DE); Andreas Nabers, Bochum (DE); Jonas Schartner, Herne (DE); Carsten Kötting, Bochum (DE)

(73) Assignee: betaSENSE GmbH, Bochum (DE)

( * ) Notice: Subject to any disclaimer, the term of this patent is extended or adjusted under 35 U.S.C. 154(b) by 652 days.

(21) Appl. No.: 16/847,236

(22) Filed: Apr. 13, 2020

(65) Prior Publication Data
US 2020/0240908 A1 Jul. 30, 2020

Related U.S. Application Data

(62) Division of application No. 15/113,128, filed as application No. PCT/EP2015/052945 on Feb. 12, 2015, now Pat. No. 11,073,470.

(30) Foreign Application Priority Data

Feb. 14, 2014 (EP) ..................................... 14155138

(51) Int. Cl.
G01N 21/3577 (2014.01)
G01N 21/552 (2014.01)
G01N 21/64 (2006.01)
G01N 33/68 (2006.01)
G01N 21/05 (2006.01)

(52) U.S. Cl.
CPC ....... *G01N 21/3577* (2013.01); *G01N 21/552* (2013.01); *G01N 21/6428* (2013.01); *G01N 21/6458* (2013.01); *G01N 33/6896* (2013.01); *G01N 21/05* (2013.01); *G01N 2021/6421* (2013.01); *G01N 2800/2821* (2013.01); *G01N 2800/2835* (2013.01)

(58) Field of Classification Search
CPC ............ G01N 21/3577; G01N 21/552; G01N 21/6458; G01N 33/6896; G01N 21/6428; G01N 2021/6421; G01N 21/05; G01N 2800/2821; G01N 2800/2835
See application file for complete search history.

(56) References Cited

U.S. PATENT DOCUMENTS

| | | | |
|---|---|---|---|
| 6,110,446 A | 8/2000 | Prencipe et al. | |
| 8,883,010 B2 * | 11/2014 | Chandrasekaran | A61K 31/35 549/243 |
| 9,146,229 B2 * | 9/2015 | Zhang | H01L 21/02164 |
| 11,073,470 B2 * | 7/2021 | Gerwert | G01N 21/552 |
| 2002/0197731 A1 | 12/2002 | McFarland et al. | |
| 2003/0157725 A1 * | 8/2003 | Franzen | G01N 21/552 436/171 |
| 2004/0121491 A1 | 6/2004 | Marchand-Brynaert et al. | |
| 2004/0180147 A1 | 9/2004 | Parikh et al. | |
| 2005/0282925 A1 | 12/2005 | Schlenoff et al. | |
| 2007/0003921 A1 * | 1/2007 | Andrus | G01N 21/35 702/19 |
| 2009/0028869 A1 * | 1/2009 | Dodel | C07K 16/18 530/387.9 |
| 2009/0202515 A1 * | 8/2009 | Yoneyama | G01N 33/5058 435/200 |
| 2012/0021486 A1 | 1/2012 | Dinu et al. | |
| 2012/0170023 A1 | 7/2012 | Szobota et al. | |
| 2012/0309943 A1 | 12/2012 | Kumada et al. | |
| 2013/0022620 A1 | 1/2013 | Schmidt | |
| 2014/0288093 A1 | 9/2014 | Krainc et al. | |
| 2015/0140003 A1 | 5/2015 | Kaluza et al. | |
| 2015/0309045 A1 | 10/2015 | Picotti et al. | |
| 2016/0279238 A1 | 9/2016 | Neumann et al. | |
| 2017/0010212 A1 | 1/2017 | Gerwert et al. | |
| 2018/0328835 A1 | 11/2018 | Bauer et al. | |
| 2019/0277863 A1 | 9/2019 | Barbour | |
| 2019/0285650 A1 | 9/2019 | Gerwert et al. | |
| 2019/0285651 A1 | 9/2019 | Gerwert et al. | |
| 2019/0369015 A1 | 12/2019 | Ismail et al. | |
| 2020/0141864 A1 | 5/2020 | Ismail et al. | |

(Continued)

FOREIGN PATENT DOCUMENTS

| | | | | |
|---|---|---|---|---|
| CA | 2882673 | * | 2/2014 | ............ G01N 21/35 |
| EP | 1214594 B1 | | 2/2006 | |
| EP | 1806574 A1 | | 7/2007 | |

(Continued)

OTHER PUBLICATIONS

Eurogentec, 2011 Price List Covance Antibodies, p. 2 (alpha-Synuclein (4B12) Monoclonal Antibody (SIGNET) catalog # SIG-39730 et seq.*
Payne ("Fourier Transform IR Spectroscopy of Collagen and Gelatin Solutions: Deconvolution of the Amide I Band for Conformational Studies", Biopolymers, vol. 27, 1749-1760 (1988).*
Meredith ("Protein Denaturation and Aggregation; Cellular Responses to Denatured and Aggregated Proteins", Ann. N.Y. Acad. Sci. 1066: 181-221 (2005).*
Bassan. Resonant Mie Scattering (RMieS) correction of infrared spectra from highly scattering biological samples, Analyst, 2010, 135, 268-277.*
Schwaighofer, "Beyond Fourier Transform Infrared Spectroscopy: External Cavity Quantum Cascade Laser-Based Mid-infrared Transmission Spectroscopy of Proteins in the Amide I and Amide II Region", Anal. Chem. 2018, 90, 7072-7079.*

(Continued)

*Primary Examiner* — Ann Montgomery
(74) *Attorney, Agent, or Firm* — Mandar A. Joshi; Bozicevic, Field & Fransic LLP

(57) ABSTRACT

Provided herein is a biosensor for conformation and secondary structure analysis, notably for the direct non-invasive qualitative secondary structure analysis of a single selected protein within a complex mixture, as e.g. a body fluid, by vibrational spectroscopic methods. For the analysis it is not required that the selected substance be isolated, concentrated, or pretreated by a special preparative procedure.

16 Claims, 15 Drawing Sheets

(56) References Cited

U.S. PATENT DOCUMENTS

2020/0141866 A1    5/2020    Gerwert et al.

FOREIGN PATENT DOCUMENTS

| EP | 2490029 A1 | 8/2012 | |
|---|---|---|---|
| EP | 2700933 | 2/2014 | |
| JP | 2002040023 | 2/2002 | |
| WO | 0070345 A1 | 11/2000 | |
| WO | 0201202 A1 | 1/2002 | |
| WO | 02056018 A1 | 7/2002 | |
| WO | WO 02/056018 * | 7/2002 | ........... G01N 33/543 |
| WO | 2007131997 A1 | 11/2007 | |
| WO | 2015121339 A1 | 8/2015 | |
| WO | 2018/091738 | 5/2018 | |
| WO | 2018091743 A1 | 5/2018 | |
| WO | 2018/219969 | 12/2018 | |

OTHER PUBLICATIONS

Bennett et al., (2004) "Neurofibrillary Tangles Mediate the Association of Amyloid Load With Clinical Alzheimer Disease and Level of Cognitive Function", Arch. Neurol. 61(3):378-84.

Piling et al. (2016) "Fundamental developments in infrared spectroscopic imaging for biomedical applications", The Royal Society of Chemistry, Chem. Soc., 45:1935-1957.

Syad & Devi (2015) "Assessment of Anti-Amyloidogenic Activity of Marine Red Alga G. Acerosa Against Alzheimer's Beta-Amyloid Peptide 25-35", Neurological Research 37(1):14-22.

Koetting et al., (2010) "Label-Free Screening of Drug-Protein Interactions by Time-Resolved Fourier Transform Infrared Spectroscopic Assays Exemplified by Ras Interactions" Applied Spectroscopy, 64:9 967-972.

BioLegend, Product Data Sheet, "Purified anti-a-Synuclein, 103-108", (2015), 2 pages.

Eurogentec, "2011 Price List", Covance Antibodies, https://www.yumpu.com/en/document/read/8051743/2011-price-list-covance-antibodies-eurogentec, (2011), 2 pages.

Fjorback et al., "Determination of alpha-synuclein concentration in human plasma using ELISA", Scandinavian Journal of Clinical and Laboratory Investigation, 2007, pp. 431-435, vol. 67.

Heiser et al., "Inhibition of huntingtin fibrillogenesis by specific antibodies and small molecules: Implications for Huntington's disease therapy", PNAS, 2000, pp. 6739-6744, vol. 97, No. 12.

Perchiacca et al., "Structure-based design of conformation- and sequence-specific antibodies against amyloid β", PNAS, 2012, pp. 84-89, vol. 109, No. 1.

Bard et al., (Proc. Nat. Acad. Sci. USA 100(4): 2023-2028, 2003) (Year: 2003).

Product Information for Sigma A8978 Anti-beta-amyloid (13-28) antibody, downloaded from https://www.sigmaaldrich.com/catalog/products/sigma/a8978?lang=en&region=US on Dec. 12, 2018 (Year: 2018).

Devouge et al., "Surface functionalization of germanium ATR devices for use in FTIR-biosensors", J Colloid Inter. Sci. 2009, 32: 408-415.

Konishi et al., "Antibodies to bovine serum albumin in human sera: problems and solutions with casein-based ELISA in the detection of natural Japanese encephalitis virus infections", Jpn. J Infect. Dis., 2010, 63: 296-298.

Schartner et al., "Universal Method for Protein Immobilization on Chemically Functionalized Germanium Investigated by ATR-FTIR Difference Spectroscopy", Journal of the American Chemical Society, Jan. 9, 2013, pp. 4079-4087, vol. 135, No. 10.

Xiao et al., "Enzyme-linked immunosorbent assay (ELISA) and blocking with bovine serum albumin (BSA)—not all BSAs are alike", J Immunol. Methods 2012, 384(1-2): 148-151.

Nabers et al., "An infrared sensor analysing label-free the secondary structure of the Abeta peptide in presence of complex fluids", Journal of Biophotonics, 2015, pp. 224-234, vol. 9:3.

Nabers et al., "Amyloid-β-Secondary Structure Distribution in Cerebrospinal Fluid and Blood Measured by an Immuno-Infrared-Sensor: A Biomarker Candidate for Alzheimer's Disease, analytical chemistry", 2016, pp. 2755-2762, vol. 88.

Kleiren, "Towards an Early Diagnosis of Alzheimer's Disease: Development of an ATR-FTIR Biosensor for the the Dectection of Aβ Toxic Conformations", 2013, Thesis, Universite Libre de Bruxe, pp. 1-162.

Van Cauwenberge et al., "Development of a New Low-Cost and Regerable Detection Device for Microbial Compounds 'MIC-ATR'", 2012, Science for a Sustainable Development, pp. 1-111.

Ataka et al., "Oriented Attachment and Membrane Reconstitution of His-Tagged Cytochrome c Oxidase to a Gold Electrode: In Situ Monitoring by Surface-Enhanced Infrared Absorption Spectroscopy", J. Am. Chem. Soc., 2004, pp. 16199-16206, vol. 126.

Badura et al., "Light-Driven Water Splitting for (Bio-)Hydrogen Production: Photosystem 2 as the Central Part of a Bioelectrochemical Device", Photochemistry and Photobiology, 2006, pp. 1385-1390, vol. 82.

Benilova et al., "The toxic Aβ oligomer and Alzheimer's disease: an emperor in need of clothes", Nature Neuroscience, Mar. 2012, pp. 349-357, vol. 15, No. 3.

Brauns et al., "Time-Resolved Infrared Spectroscopy of RNA Folding", Biophysical Journal, Nov. 2005, pp. 3523-3530, vol. 89.

Bruggink et al., "Amyloid-β oligomer detection by ELISA in cerebrospinal fluid and brain tissue", Analytical Biochemistry, 2013, pp. 112-120, vol. 433.

Byrne et al., "Antibody-Based Sensors: Principles, Problems and Potential for Detection of Pathogens and Associated Toxins", Sensors, 2009, pp. 4407-4445, vol. 9.

Cerf et al., "Antiparallel β-sheet: a signature structure of the oligomeric amyloid β-peptide", Biochem. J., 2009, pp. 415-423, vol. 421.

Devouge et al., "A practical molecular clip for immobilization of receptors and biomolecules on devices' surface: Synthesis, grafting protocol and analytical assay", Bioorganic & Medicinal Chemistry Letters, 2005, pp. 3252-3256, vol. 15.

Elfrink et al., "Structural changes of membrane-anchored native PrPC", PNAS, Aug. 5, 2008, pp. 10815-10819, vol. 105, No. 31.

Elfrink et al., "Interaction of the cellular prion protein with raft-like lipid membranes", Biol. Chem., Jan. 2007, pp. 79-89, vol. 388.

Frost et al., "Conformational Diversity of Wild-type Tau Fibrils Specified by Templated Conformation Change", The Journal of Biological Chemistry, Feb. 6, 2009, pp. 3546-3551, vol. 284, No. 6.

Funke, "Detection of Soluble Amyloid-β Oligomers and Insoluble High-Molecular-Weight Particles in CSF: Development of Methods with Potential for Diagnosis and Therapy Monitoring of Alzheimer's Disease", International Journal of Alzheimer's Disease, Sep. 11, 2011, pp. 1-8, vol. 2011.

Funke et al., "A Unique Sequence Motif in the 54-kDa Subunit of the Chloroplast Signal Recognition Particle Mediates Binding to the 43-kDa Subunit*", The Journal of Biological Chemistry, Mar. 11, 2005, pp. 8912-8917, vol. 280, No. 10.

Funke et al., "Single-Particle Detection System for Aβ Aggregates: Adaptation of Surface-Fluorescence Intensity Distribution Analysis to Laser Scanning Microscopy", Rejuvenation Research, 2010, pp. 206-209, vol. 13, No. 2-3.

Goldsztein, "Development of a new type of biosensors based on ATR-FTIR Spectroscopy", Thesis, Sep. 13, 2012, pp. 1-84.

Goldzstein et al., "Ligand-receptor interactions in complex media: A new type of biosensors for the detection of coagulation factor VIII", Biosensors and Bioelectronics, 2009, pp. 1831-1836, vol. 24.

Güldenhaupt et al., "Secondary structure of lipidated Ras bound to a lipid bilayer", FEBS Journal, 2008, pp. 5910-5918, vol. 275.

Habicht et al., "Directed selection of a conformational antibody domain that prevents mature amyloid fibril formation by stabilizing Aβ protofibrils", PNAS, Dec. 4, 2007, pp. 19232-19237, vol. 104, No. 49.

Han et al., "Formation of Alkanethiol Monolayer on Ge(111)", J. Am. Chem. Soc., 2001, pp. 2422-2425, vol. 123.

Hofer et al., "Structural Investigation of Biological Material in Aqueous Environment by Means of Infrared-ATR Spectroscopy", Biophys. Struct. Mech., 1979, pp. 67-80, vol. 6.

(56) References Cited

OTHER PUBLICATIONS

Kleiren et al., "Development of a quantitative and conformation-sensitive ATR-FTIR biosensor for Alzheimer's disease: The effect of deuteration on the detection of the Aβ peptide", Spectroscopy, 2010, pp. 61-66, vol. 24.

Kotting et al., "Time-resolved FTIR spectroscopy for monitoring protein dynamics exemplified by functional studies of Ras protein bound to a lipid bilayer", Chemical Physics, 2012, pp. 72-83, vol. 396.

Laganowsky et al., "Atomic View of a Toxic Amylid Small Oligomer", Science, Mar. 9, 2012, pp. 1228-1231, vol. 335.

Löfås, "A Novel Hydrogel Matrix on Gold Surfaces in Surface Plasmon Resonance Sensors for Fast and Efficient Covalent Immobilization of Ligands", J. Chem. Soc., Chem. Commun., 1990, pp. 1526-1528.

Loscutoff et al., "Reactivity of the Germanium Surface: Chemical Passivation and Functionalization", Annu. Rev. Phys. Chem., 2006, pp. 467-495, vol. 57.

Matijašević et al., "In Situ ATR FTIR Monitoring of the Formation of Functionalized Mono- and Multilayers on Germanium Substrate: from 7-Octenyltrichlorosilane to 7-Carboxylsilane", Langmuir, 2008, pp. 2588-2596, vol. 24.

Morgado et al., "Molecular basis of β-amyloid oligomer recognition with a conformational antibody fragment", PNAS, Jul. 31, 2012, pp. 12503-12508, vol. 109, No. 31.

Ollesch et al., "FTIR spectroscopy of biofluids revisited: an automated approach to spectral biomarker identification", Analyst, 2013, pp. 4092-4102, vol. 138.

Ollesch et al., "Prion Protein α-to-β Transition Monitored by Time-Resolved Fourier Transform Infrared Spectroscopy", Applied Spectroscopy, 2007, pp. 1-7, vol. 61, No. 10.

Olsztyńska-Janus et al., "Spectroscopic techniques in the study of human tissues and their components. Part I: IR spectroscopy", Acta of Bioengineering and Biomechanics, 2012, pp. 101-115, vol. 14, No. 3.

Pinkerneil et al., "Surface-Attached Polyhistidine-Tag Proteins Characterized by FTIR Difference Spectroscopy", ChemPhysChem, 2012, pp. 2649-2653, vol. 13.

Punzet et al., "Determination of surface concentrations of individual molecule-layers used in nanoscale biosensors by in-situ ATR-FTIR spectroscopy", Institute of Biophysical Chemistry, University of Vienna, Austria, 2012, pp. 1-15.

Yu et al., "Structural Characterization of a Soluble Amyloid β-Peptide Oligomer", Biochemistry, 2009, pp. 1870-1877, vol. 48.

Smith et al., "Covalent Attachment of a Nickel Nitrilotriacetic Acid Group to a Germanium Attenuated Total Reflectance Element", Langmuir, 2004, pp. 1184-1188, vol. 20.

Venkataramani et al., "Antibody 9D5 Recognizes Oligomeric Pyroglutamate Amyloid-β in a Fraction of Amyloid-β Deposits in Alzheimer's Disease without Cross-Reeactivity with other Protein Aggregates", Journal of Alzheimer's Disease, 2012, pp. 361-371, vol. 29.

Voue et al., "Biochemical Interaction Analysis on ATR Devices: A Wet Chemistry Approach for Surface Functionalization", Langmuir, 2007, pp. 949-955, vol. 23.

Wang-Dietrich et al., "The Amyloid-β Oligomer Count in Cerebrospinal Fluid is a Biomarker for Alzheimer's Disease," Journal of Alzheimer's Disease, 2013, pp. 985-994, vol. 34.

Wiltfang et al., "Amyloid β peptide ratio 42/40 but not Aβ42 correlates with phospho-Tau in patients with low- and high-CSF AB40 load", Journal of Neurochemistry, 2007, pp. 1053-1059, vol. 101, DOI: 10.1111/i.1471-4159.2006.04404.x.

Wischik et al., "Tau Aggregation Inhibitor Therapy: An Exploratory Phase 2 Study in Mild or Moderate Alzheimer's Disease", Journal of Alzheimer's Disease, 2015, pp. 705-720, vol. 4, DOI: 10.3233/JAD-142874.

Wischik et al., "Selective inhibition of Alzheimer disease-like tau aggregation by phenothiazines", Proc. Natl. Acad. Sci. USA, Oct. 2006, pp. 11213-11218, vol. 93.

Yang et al., "Tau protein aggregation in the frontal and entorhinal cortices as a function of aging", Developmental Brain Research, 2005, pp. 127-138, vol. 156.

Yao et al., "Learning from berberine: Treating chronic diseases through multiple targets", Sci China Life Sci, 2015, pp. 854-859, vol. 58, No. 9, DOI: 10.1007/s11427-013-4568-z.

Zhu et al., "Berberine chloride can ameliorate the spatial memory impairment and increase the expression of interleukin-Ibeta and inducible nitric oxide synthase in the rat model of Alzheimer's disease", BMC Neuroscience, 2006, vol. 7, No. 78, DOI: 10.1186/1471-2202-7-78.

Giehm et al. (2010) "Strategies to Increase the Reproducibility of Protein Fibrillization in Plate Reader Assays" Analytical Biochemistry 400:270-281.

Stefan Barghorn et al., Tau Paired Helical Filaments from Alzheimer's Disease Brain and Assembled in Vitro Are Based on β-Structure in the Core Domain, Biochemistry, Jan. 16, 2004, 43, 1694-1703.

Ahmed et al., "Berberine and neurodegeneration: A review of literature", Pharmacological Reports, 2015, pp. 970-979, vol. 67.

Akoury et al., "Mechanic Basis of Phenothiazine-Driven Inhibition of Tau Aggregation", Angew. Chem. Int. Ed., 2013, pp. 3511-3515, vol. 52.

Alzheimer, Allg. Z. Psychiatrie Psychisch-gerichtl. Med., 1907, pp. 146-148, vol. 64.

Andreasen et al., "Cerebrospinal fluid tau protein as a biochemical marker for Alzheimer's disease: a community based follow up study", J. Neurol Neurosurg Psychiatry, 1998, pp. 298-305, vol. 64.

Baddeley et al., "Complex Disposition of Methylthioninium Redox Forms Determines Efficacy in Tau Aggregation Inhibitor Therapy for Alzheimer's Disease", J Pharmacol Exp Ther, Jan. 2015, pp. 110-118, vol. 352.

Blennow et al., "Evolution of Aβ42 and Aβ40 levels and Aβ42/Aβ40 ratio in plasma during progression of Alzheimer's disease: A multicenter assessment", The Journal of Nutrition Health and Aging, Mar. 2009, pp. 205-208, vol. 13, No. 3, DOI: 10.1007/s12603-009-0059-0.

Braak et al., "Neuropathological stageing of Alzheimer-related changes", Acta Neuropathol, 1991, pp. 239-259, vol. 82.

Campisi et al., "Effect of Berberine and Berberis aetnensis C. Presl. Alkaloid Extract on Glutamate-evoked Tissue Transglutaminase Up-regulation in Astroglial Cell Cultures", Phytother. Res., 2011, pp. 816-820, vol. 25.

Cavallucci et al., "Aβ Toxicity in Alzheimer's Disease", Mol Neurobiol, 2012, pp. 366-378, vol. 45.

Cedernaes et al., "Efficacy of antibody-based therapies to treat Alzheimer's disease: Just a matter of timing?", Experimental Gerontology, 2014, pp. 104-106, vol. 57.

Cerf et al., "Antiparallel β-sheet: a signature structure of the oligomeric amyloid β-peptide", Biochem. J., 2009, pp. 415-423, vol. 421 . . . DOI: 10.1042/BJ20090379.

Chiba, "Emerging Therapeutic Strategies in Alzheimer's Disease", IntechOpen, 2013, Chapter 9, pp. 181-225, DOI: 10.5772/55293.

Coomaraswamy et al., "Modeling familial Danish dementia in mice supports the concept of the amyloid hypothesis of Alzheimer's disease", PNAS, Apr. 27, 2010, pp. 7969-7974, vol. 107, No. 17, DOI: 10.1073/pnas.1001056107.

Cummings, "Biomarkers in Alzheimer's disease drug development", Alzheimer's & Dementia: The Journal of the Alzheimer's Association, May 2011, pp. e13-e44, vol. 7, Issue 2, DOI: 10.1016/j.jatz.2010.06.004.

Doecke et al., "Blood-Based Protein Biomarkers for Diagnosis of Alzheimer Disease", Arch Neurol., 2012, pp. 1318-1325, vol. 69, No. 10, DOI: 10.1001/archneurol.2012.1282.

Emre, "Switching cholinesterase inhibitors in patients with Alzheimer's disease", ICP Supplement, Jun. 2002, vol. 127.

Evora, "Methylene Blue is a Guanylate Cyclase Inhibitor That Does Not Interfere with Nitric Oxide Synthesis", Texas Heart Institute Journal, Feb. 2016, vol. 43, No. 1, DOI: 10.14503/THIJ-15-5629.

Fändrich et al., "Structural Polymorphism of Alzheimer Aβ and other amyloid fibrils", Prion, Apr./May/Jun. 2009, pp. 89-93, vol. 3, No. 2.

(56) References Cited

OTHER PUBLICATIONS

Fiandaca et al., "Plasma 24-metabolite Panel Predicts Preclinical Transition to Clinical Stages of Alzheimer's Disease", Frontiers in Neurology, Nov. 2015, pp. 1-13, vol. 6, Article 237, DOI: 10.3389/fneur.2015.00237.

Gabelle et al., "Decreased sAβPPβ, Aβ38, and Aβ40 Cerebrospinal Fluid Levels in Frontotemporal Dementia", Journal of Alzheimer's Disease, 2011, pp. 553-563, vol. 26, No. 563, HAL ID: hal-00635931.

Glabe, "Structural Classification of Toxic Amyloid Oligomers", The Journal of Biological Chemistry, Oct. 31, 2008, pp. 29639-29643, vol. 283, No. 44, DOI: 10.1074/jbc.R800016200.

Greenberg et al., "Improving Alzheimer's disease phase II clinical trials", Alzheimer's & Dementia, 2013, pp. 39-49, vol. 9.

Haass et al., "Soluble protein oligomers in neurodegeneration: lessons from the Alzheimer's amyloid β-peptide", Nature Reviews Molecular Cell Biology, Feb. 2007, pp. 101-112, vol. 8.

Harrington et al., "Cellular Models of Aggregation-dependent Template-directed Proteolysis to Characterize Tau Aggregation Inhibitors for Treatment of Alzheimer Disease", The Journal of Biological Chemistry, Apr. 24, 2015, pp. 10862-10875, vol. 290, No. 17, DOI: 10.1074/jbc.M114.6161029.

Hulsemann et al., "Biofunctionalized Silica Nanoparticles: Standards in Amyloid-β Oligomer-Based Diagnosis of Alzheimer's Disease", Journal of Alzheimer's Disease, 2016, pp. 79-88, vol. 54, DOI: 10.3233/JAD-160253.

Imbimbo, "Why Did Tarenflurbil Fail in Alzheimer's Disease?", Journal of Alzheimer's Disease, 2009, pp. 757-760, vol. 17, DOI: 10.3233/JAD-2009-1092.

Kötting et al., "Proteins in Action Monitored by Time-Resolved FTIR Spectroscopy", ChemPhysChem, 2005, pp. 881-888, vol. 6, DOI: 10.1002/cphc.200400504.

Kolarova et al., "Structure and Pathology of Tau Protein in Alzheimer Disease", International Journal of Alzheimer's Disease, 2012, Article ID 731526, 13 pages, DOI: 10.1155/2012/731526.

Kühbach et al., "Application of an Amyloid Beta Oligomer Standard in the sFIDA Assay", Frontiers in Neuroscience, Jan. 19, 2016, vol. 10, Article 8, DOI: 10.3389/fnins.2016.00008.

Lee, B. et al., "Phellodendron amurense and Its Major Alkaloid Compound, Berberine Ameliorates Scopolamine-Induced Neuronal Impairment and Memory Dysfunction in Rats", Korean J Physiol Pharmacol, Apr. 2012, pp. 79-89, vol. 16. DOI: 10.4196/kjpp.2012.16.2.79.

Lee, V. et al., "Neurodegenerative Tauopathies: Human Disease and Transgenic Mouse Models", Neuron, Nov. 1999, pp. 507-510, vol. 24.

Lin et al., "A Modified Infrared Spectrometer with High Time Resolution and Its Application for Investigating Fast Conformational Changes of the GTPase Ras", Applied Spectroscopy, 2014, pp. 531-325, vol. 68, No. 5.

Lo et al., "Longitudinal Change of Biomarkers in Cognitive Decline", Arch Neurol, 2011, pp. 1257-1266, vol. 68, No. 10, DOI: 10.1001/archneurol.2011.123.

Mapstone et al., "Plasma phospholipids identify antecedent memory impairment in older adults", Nat Med., Apr. 2014, pp. 415-418, vol. 20, No. 4, DOI: 10.1038/nm.3466.

Nabers et al., "Amyloid-β-Secondary Structure Distribution in Cerebrospinal Fluid and Blood Measured by an Immuno-Infrared-Sensor: A Biomarker Candidate for Alzheimer's Disease", Anal. Chem., 2016, pp. 2755-2762, vol. 88, DOI: 10.1021/acs.analchem.5b04286.

Nabers et al., "An infrared sensor analysing label-free the secondary structure of the Abeta peptide in presence of complex fluids", J. Biophotonics, 2016, pp. 224-234, vol. 9, No. 3, DOI: 10.1002/jbio.201400145.

Necula et al., "Methylene Blue Inhibits Amyloid Aβ Oligomerization by Promoting Fibrillization", Biochemistry, 2007, pp. 8850-8860, vol. 46, DOI: 10.1021/b1700411k.

Nisha Syad et al., "Assessment of anti-amyloidogenic activity of marine red alga G. acerosa against Alzheimer's beta-amyloid peptide 25-35", Neurological Research, 2015, pp. 14-22, vol. 37, No. 1, DOI: 10.1179/1743132814Y.0000000422.

Pickhardt et al., "Identification of small molecule inhibitors of Tau aggregation by targeting monomeric Tau as a potential therapeutic approach for Tauopathies", Curr Alzheimer Res., 2015, pp. 814-828, vol. 12, No. 9.

Prince et al., "World Alzheimer Report 2015 the Global Impact of Dementia: An Analysis of Prevalence, Incidence, Cost and Trends", Alzheimer's Disease International, 2015.

Ramsay et al., "Methylene blue and serotonin toxicity: inhibition of monoamine oxidase A (MAO A) confirms a theoretical prediction", British Journal of Pharmacology, 2007, pp. 946-951, vol. 152.

Rey-Funes et al., "Methylene blue prevents retinal damage in an experimental model of ischemic proliferative retinopathy", Am J Physiol Regul Integr Comp Physiol, 2016, pp. R1011-R1019, vol. 310.

Sachs et al., "Paired β-sheet struction of an Aβ(1-40) amyloid fibril revealed by electron microscopy", PNAS, May 27, 2008, pp. 7462-7466, vol. 105, No. 21, DOI: 10.1073/pnas.0712290105.

Sarroukh et al., "Transformation of amyloid β(1-40) oligomers into fibrils is characterized by a major change in secondary structure", Cell. Mol. Life Sci., 2010, DOI: 10.007/s00018-010-0529-x.

Schartner et al., "Immoblization of Proteins in their Physiological Active State at Functionalized Thiol Monolayers on ATR-Germanium Crystals", ChemBioChem, 2014, pp. 2529-2534, vol. 15, DOI: 10.1002/cbic.201402478.

Šimić et al., "Tau Protein Hyperphosphorylation and Aggregation in Alzheimer's Disease and Other Tauopathies, and Possible Neuroprotective Strategies", Biomolecules, 2016, vol. 6, No. 6, DOI: 10.3390/biom6010006.

Thal et al., " Sequence of Aβ-Protein Deposition in the Human Medial Temporal Lobe", "Journal of Neuropathology and Experimental Neurology", Aug. 2000, pp. 733-748, vol. 59, No. 8.

Thal et al., "The Development of Amyloid β Protein Deposits in the Aged Brain", Sci Aging Knowl. Environ., Mar. 8, 2006, vol. 2006, No. 6, DOI: 10.1126/sageke.206.6.re1.

Thorsett et al., "Therapeutic Approaches to Alzheimer's Disease", Current Opinion in Chemical Biology, 2000, pp. 377-382, vol. 4.

Wang et al., "Tau in physiology and pathology", Nat Rev Neurosci., Jan. 2016, pp. 5-21, vol. 17, No. 1, DOI: 10.1038/nrn.2015.1.

Lee et al., (2001) "Neurodegenerative Tauopathies: Human Disease and Transgenic Mouse Models", Annual Rev. of Neuroscience 24:1121-1159.

NPL search history (2020) 1 page.

Skibiniski and Finkbeiner, (2011) Drug discovery in Parkinson's disease-update and developments in the use of cellular models, Int J. High Throughput Screen, vol. 2, pp. 15-25.

Griffiths & Haseth (2007) "Fourier Transformation Infrared Spectrometry", Wiley-Interscience, 2:1-44.

Hillen et al., (2010) "Generation and Therapeutic Efficacy of Highly Oligomer-Specific B-Amyloid Antibodies", The Journal of Neuroscience, 30(31): 10369-10379.

\* cited by examiner

ATTENUATED TOTAL REFLECTANCE-BASED BIOSENSOR FOR CONFORMATION AND SECONDARY STRUCTURE ANALYSIS

CROSS-REFERENCE TO RELATED APPLICATIONS

This application is a divisional application of U.S. patent application Ser. No. 15/113,128, filed Jul. 21, 2016, which is the United States national phase of International Application No. PCT/EP2015/052945 filed Feb. 12, 2015, and claims priority to European Patent Application No. 14155138.2 filed Feb. 14, 2014, the disclosures of which are hereby incorporated in their entirety by reference.

The invention provides a biosensor for conformation and secondary structure analysis, notably for the direct non-invasive qualitative secondary structure analysis of a single selected protein within a complex mixture, as e.g. a body fluid, by vibrational spectroscopic methods. For the analysis it is not required that the selected substance be isolated, concentrated, or pretreated by a special preparative procedure

BACKGROUND OF THE INVENTION

Quantitative methods for the detection of biomarker candidates in bodily fluids are enzyme-linked immune-sorbent assays (ELISA), surface plasmon resonance spectroscopy (SPR), surface fluorescence intensity distribution analysis (sFIDA) or mass spectroscopy techniques. These techniques do not provide direct information about the secondary structure of the analytes. Antibody based methods like ELISA or SPR may be complemented with conformation sensitive antibodies, so that structure information of particularly one conformation can be derived indirectly (I. Morgado et al., Proc. Natl. Acad. Sci., 109(31): 12503-12508 (2012); Venkataramani et al., JAD 29(2):361-371 (2012)). Using these conformation sensitive antibodies, our studies demonstrated that only the specific secondary structure was detected. Thus, a sample discrimination based on the specific structural composition of an analyzed compound is not possible; all detectable conformations are present in natural samples, but the composition varies in e.g. a disease. The later described discrimination requires a structure independent antibody, because the recorded signal has to reflect concentration differences of the observed structures. sFIDA detects candidate biomarker dimers or oligomers by using identical immobilization and detection antibodies. However, sFIDA does not detect structure information (S. Funke et al., Rejuvenation Res., 13(2-3):206-209 (2010)). The secondary structure analysis of proteins by Fourier-transform infrared (FTIR-) spectroscopy and the analysis of recombinant or purified proteins after immobilization on particular attenuated total reflection (ATR-) sensor surfaces has frequently been described (J. Ollesch et al., Appl. Spectrosc., 61(10): 1025-1031 (2007); K. Elfrink, J. Ollesch et al., Proc Natl Acad Sci, 105(31):10815-10819 (2008); Frost et al., J. Biol. Chem., 284(6):3546-3551 (2009); S. Funke et al., J. Biol. Chem., 280(10):8912-7 (2005)). FTIR-spectroscopic secondary structure analysis of nucleic acids like RNA have already been published (E. Brauns and R. B. Dyer, Biophys. J., 89(5):3523-3530 (2005)). In the present state of scientific and technical knowledge no secondary structure analysis of components from complex fluids like serum, blood plasma or cerebrospinal fluid without prior isolation have been reported to date. The selective detection of specific components out of a complex body fluid by applying an ATR-flow-through sensor constitutes an innovative new development. So far this technique was only applied to isolated proteins. Internal reflection elements (IRE) of ATR-sensors typically consist of infrared permeable materials with a high refraction index. These include diamond, germanium, silicon or zinc selenide. Proteins are immobilized on these surfaces via tethered lipids (K. Elfrink, L. Nagel-Steger and D. Riesner, Biol. Chem., 388(1):79-89 (2007); K. Elfrink, J. Ollesch et al., PNAS 2008; J. Giildenhaupt et al., The FEBS Journal, 275(23):5910-5918 (2008); C. Kitting et al., Chemical Physics, 396:72-83 (2012); P. Pinkerneil et al., Chemphyschem, 13(11):2649-2653 (2012)), thiolchemistry on vapor-deposited or chemical secluded gold surfaces (Ataka et al., J. Am. Chem. Soci., 126(49):16199-16206 (2004); A. Badura et al., Photochem. and Photobiol., 82(5):1385-1390 (2006)) or silanes (B. M. Smith et al., Langmuir, 20(4):1184-1188 (2004); S. Devouge et al., Bioorg. & Med. Chem. Lett., 15(13):13252-13256 (2005); P. W. Loscutoff and S. F. Bent, Ann. Rev. Physical Chemistry, 57(1):467-495 (2006); J. Matijasevic et al., Langmuir, 24(6):2588-2596 (2008); S. Devouge et al., Journal of Colloid and Interface Science, 332(2):408-415 (2009); J. Schartner et al., J. Am. Chem. Soci., 135(10):4079-4087 (2013)). In this process, the immobilization of antibodies or other proteins on other semiconductors than germanium has been described (P. Hofer and Fringeli, Biophysics of Structure and Mechanism, 6(1):67-80 (1979); S. Lifas and B. Johnsson, J. Chem. Soc., Chem. Comm. (21):1526 (1990); B. Byrne et al., Sensors (Basel, Switzerland), 9(6):4407-4445 (2009); M. Punzet et al., Nanoscale, 4(7):2431 (2012)). Invention relevant reagents have been synthesized by the inventors. The basic silanes were published (J. Schartner et al., J. Am. Chem. Soc., 135(10):4079-4087 (2013)), but the main application, the immobilization of antibodies through free lysine residues and short chain triethoxysilanes, has not been described so far. The antibody immobilization through proteinogenic lysines on other succinimidylester has been reported (S. Lifas and B. Johnsson, J. Chem. Soci., Chem. Comm. (21):1526 (1990); EP-B-1214594 and WO2000070345). However, the analysis was not performed by IR spectroscopy, therefore protein secondary structure analysis was not performed. The use of functionalized short-chain trialkoxysilanes (such as N-(4,4,4-triethoxysilanebutyl)succinamic acid 2,5-dioxopyrrolidin-1-yl ester) for covalent protein immobilization has not been reported.

In a further approach, the ATR-IRE were silanized and coupled with biotin resulting in an avidin/streptavidin sensor without any secondary structure analysis (M. Voue et al., Langmuir, 23(2):949-955 (2007)). Here the sensor surface was modified in a more complex workflow and through aggressive chemicals, which can influence and change the secondary structure of the analyte. It was shown that the presented preparation is not appropriate to generate the proposed sensor for the analysis of a selected protein in a complex body fluid under physiological conditions (Kleiren et al., Spectroscopy—An International Journal, 24 (1-2, SI): 61-66. (2010)). Apart from Voue (M. Voue et al., Langmuir, 23(2):949-955 (2007); S. Devouge et al., Journal of Colloid and Interface Science, 332(2):408-415 (2009)), 02/056018 and EP-A-1806574 disclose an optical element suitable for the analysis of ligand-receptor interactions.

WO 02/056018 refers explicitly to a device for the investigation of ligand interactions with a receptor, consisting of an attenuated total internal reflection element, transparent in the infrared and of which at least one surface is chemically activated by oxidation, hydroxylation or reduction and covalently grafted with a long chain silane derivative capable of immobilizing the receptor. The attenuated total internal reflection element is made from a material selected from germanium, silicon, ZnSe, ZnS, and AM-TIR. The device is suitable for studying ligand-receptor interactions. Further WO 02/001202 mentions the combination of ATR-IR-spectroscopy with polarized radiation and refractometric measurements.

EP-A-1806574 discloses a device suitable for the investigation of ligand-receptor interactions, in particular for the investigation of an analyte-target interaction such as biological and chemical molecules and organic components and their interaction with surfaces, consisting of an attenuated total internal reflection element, transparent in the infrared and of which at least one surface is reduced and covalently grafted with an alkene able to immobilize the receptor, wherein said alkene is optionally substituted by one or more substituent selected from alkyl, haloalkyl, halo, alkenyl, cyano, epoxy, thio, amino, hydroxyl, isocyano, isothiocyano, carboxy, polyalkoxy, alkylarylsulphoxy-polyalkoxy, or heteroaryloxycarbonylakyl-polyalkoxy. The attenuated total internal reflection element is made from germanium, notably a crystal having a trapezoidal, hemi-cylindrical, fiber or rod shaped geometry, or polyhedral form. The device is suitable for studying ligand-receptor interactions, in particular biological molecules or organic components or their interactions or complexations or reactions with biological molecules or organic components or water-soluble molecules at or in the grafted organic molecule.

WO 02/001202 and US2012/0309943 discloses the principal generation of an antibody-support by, for example, silanes.

WO 07/131997 refers to an ATR-IR-measurement setup, in which the sample is sustained in a specified distance to the ATR-surface without direct contact. A spectroscopically inert medium is intended as spacer.

Conventional spectroscopy requires a multistage preparation of complex samples, to isolate the single analyte in a high concentration for analysis. Secondary structures may change during preparation.

SPR and ELISA methods quantify specific components with high sensitivity in complex media, but cannot gather secondary structure information. These are highly sensitive, but purely quantitative methods. Conformationally sensitive (implying conformational specificity) antibodies are generally insensitive for transition states of the analyte structure (S. A. Funke, International Journal of Alzheimer's Disease, 2011:1-8 (2011); K. A. Bruggink et al., Analytical Biochemistry, 433(2):112-120 (2013)), which are nevertheless relevant for a disease (I. Benilova et al., Nature Neuroscience, 15(3):349-357 (2012)).

IR compatible materials reported for antibody binding comprise silicon, diamond and germanium. Silicon absorbs IR radiation in the analyzed spectral fingerprint range. Diamond is an expensive material which prevents the realization of larger detector areas for an increased sensitivity. The refractive indices of silicon and diamond are lower than of germanium, which reflects in a decreased signal/noise ratio as compared to the latter.

By the selection of identical antibodies for capture and detection, sFIDA is sensitive for di- or oligomeric aggregates (L. Wang-Dietrich et al., JAD, 34(4):985-994 (2013)). The secondary structure is not directly analyzed.

The secondary structure analysis of proteins is a standard application of an array of techniques (UV/Vis circular dichroism spectroscopy, IR spectroscopy, NMR spectroscopy). Altogether, highly pure and concentrated proteins are required for analysis.

Protein immobilization via silanes is disclosed in EP-A-1806574 and WO 02/056018 for the analysis of receptor-ligand interactions exclusively. Thus, reactions of and with the tethered protein were considered. The secondary structure analysis of further ligands of the tethered proteins was not considered.

A reliable diagnosis of the most relevant known protein misfolding disease, Alzheimer's, currently requires an advanced state of the disease. Current biomarker analysis is based on quantitative ELISA. The structural transition of e.g. the amyloid-beta (Aß) peptide during disease progression is thought to be initiated long before clinical symptoms of the patient. This considered, the structural analysis of the biomarker candidate not only offers potential for supplementing established diagnostics, but—even more important—may enable an earlier timepoint for diagnosis.

Thus, a therapy may start earlier, securing longer life quality.

SUMMARY OF THE INVENTION

The present invention provides a direct secondary structure analysis of selective components from a complex body fluid without prior isolation or concentration. It is based on a sensor element having antibodies directly immobilized thereon via short silane or thiol linkers, notably a germanium surface where the antibodies are bound covalently via a peptide bond to immobilized triethoxysilane or thiol linkers. The immunological linkage renders the germanium surface highly specific for selective substances, similar to ELISA methods. The captured substances are analyzed by infrared spectroscopy for the particular secondary structure. The potentially prognostic misfolding can be quantified. With the method the biomarker secondary structure within a complex body fluid can be specified. The sensor design enables a parallel control with an alternative spectroscopic technique, e.g. fluorescence spectroscopy. The immunologically determined high specificity for a substance enables the direct secondary structure analysis of selected biomarkers from complex fluids as e.g. cerebrospinal fluid (csf) or blood without pretreatment.

The invention thus provides:

(1) An optical sensor element for the direct analysis of the quantity and secondary structure of a macromolecular substance, wherein said infrared sensor element comprises a germanium internal reflection element being transparent in the infrared, and at least one receptor for the macromolecular substance being directly grafted to at least one surface of said internal reflection element by silanization with short silane linkers or by thiolation with short thiol linkers and reacting freely accessible amine groups of the receptor with amine-reactive groups on the short silane/thiol linkers.

(1') An infrared sensor element for the direct analysis of the quantity and secondary structure of a candidate biomarker protein undergoing conformational transitions associated with disease progression, wherein said infrared sensor element comprises a germanium internal reflection element being of trapezoid or parallelogram shape and being transparent in the infrared, and at least one receptor for the biomarker protein being an antibody capable of specific and conformationally independent binding to the candidate biomarker protein and being directly grafted to at least one surface of said internal germanium reflection element by silanization with short silane linkers or by thiolation with short thiol linkers, reacting freely accessible amine groups of said at least one receptor with amine-reactive groups on the short silane/thiol linkers, and blocking remaining amine-reactive groups on the short silane/thiol linkers with a blocking substance not cross-reacting with the candidate biomarker protein.

(2) A device for the direct analysis of the quantity and secondary structure of a macromolecular substance comprising the optical sensor of (1) or (1') above.

(3) A method for the preparation of the optical sensor element with short silane linkers of (1) above, comprising the steps of:

(a) surface activation of at least one surface of the germanium internal reflection element by oxidation, (b) grafting of short silane linkers to the activated surface obtained in step (a), and (c) covalently coupling a receptor to the internal reflection element via the amine-reactive group of the short silane linkers.

(3') A method for the preparation of the infrared sensor element with a short silane linker of any one of (1') above, comprising the steps of:

(a) surface activation of at least one surface of the internal reflection element by oxidation, (b) grafting short silane linkers to the activated surface obtained in step (a), (c) covalently coupling the receptor to the internal reflection element via the amine-reactive group of the short silane linkers, and (d) blocking remaining amine-reactive groups on the short silane linkers with the blocking substance not cross-reacting with the candidate biomarker protein.

(4) A method for the preparation of the optical sensor element with short thiol linkers of (1) above, comprising the steps of:

(a) surface activation of at least one surface of the germanium internal reflection element by reaction with HF, (b) grafting of short thiol linkers to the activated surface obtained in step (a), and (c) covalently coupling a receptor to the internal reflection element via the amine-reactive group of the short thiol linkers.

(4') A method for the preparation of the infrared sensor element with short thiol linkers of any one of claims 1 to 7 comprising the steps of:

(a) surface activation of at least one surface of the internal germanium reflection element by reaction with HF, (b) grafting of short thiol linkers to the activated surface obtained in step (a), and (c) covalently coupling the receptor to the internal reflection element via the amine-reactive group of the short thiol linkers, and (d) blocking remaining amine-reactive groups on the short thiol linkers with the blocking substance.

(5) The use of the optical sensor element of (1) above, or of the device of (2) above for determining the secondary structure, and optionally the quantity, of a macromolecular substance in a complex fluid including bodily fluids.

(5') The use of the infrared sensor element of (1') above, or the device of (2) above for determining the secondary structure, and optionally the quantity, of a candidate biomarker protein undergoing conformational transitions associated with disease progression in a complex fluid including bodily fluids.

(6) a method for determining the secondary structure, and optionally the quantity, of a macromolecular substance in a complex fluid, comprising the steps (a) conducting, in an IR cell comprising the optical sensor element of (1) above, a flux of potential macromolecular ligands for the receptor on the surface of said optical sensor;

(b) submitting an IR beam through said cell and obtaining an infrared spectrum therefrom; and (c) analyzing the obtained infrared spectrum to determine the secondary structure, and optionally the quantity, of the macromolecular substance.

(6') A method for determining the secondary structure, and optionally the quantity, of a candidate biomarker protein undergoing conformational transitions associated with disease progression in a complex fluid, comprising the steps (a) conducting, in an IR cell comprising the infrared sensor element of (1') above, a flux of potential candidate biomarker proteins for the receptor on the surface of said infrared sensor;

(b) submitting an IR beam through said cell and obtaining an infrared spectrum therefrom that has a sufficient signal to noise ratio to resolve the amide I band; and (c) analyzing the obtained infrared spectrum to determine the secondary structure, and optionally the quantity, of the candidate biomarker protein.

(7) A method for the determination of progression of a disease, in which a conformational transitions of a candidate biomarker protein is associated with disease progression, wherein a shift of the amide I band maximum of the biomarker protein is a classifier indicative for the progression of the disease. It is preferred in said method (7) that the determination of the progression of the disease is conducted by a method of (6') above, and/or that a threshold classifier with a value of 1638-1648 $cm^{-1}$ is a classifier indicative for the progression of the disease.

The optical sensory element of the invention enables the direct analysis of specific substances, particularly the secondary structure of proteins, with at least infrared and optionally fluorescence spectroscopy, without the need to isolate or concentrate the substance/the protein. This implies, that especially disease biomarker candidates are analysed not only quantitatively, but in particular regarding the secondary structure. Considering protein misfolding diseases as e.g. Alzheimer's disease, Parkinson's disease, Creutzfeldt-Jakob disease, or chorea Huntington, this information is crucially connected to the disease progression.

The advantage of the method of the invention is the direct detection of the secondary structure of biomarker candidate molecules from unprocessed, complex fluids, particularly native bodily fluids. The isolation and concentration of the substances to be detected is not necessary, it is part of the sensor and the detection technique. In contrast, conformation sensitive antibodies used in other techniques cannot quantitatively determine the secondary structure composition. Furthermore, they have a lower specificity against single secondary structure elements. The sensor element of the invention is suitable for parallel control experiments, with e.g. fluorescence techniques.

DETAILED DESCRIPTION OF THE INVENTION

Figure 1:
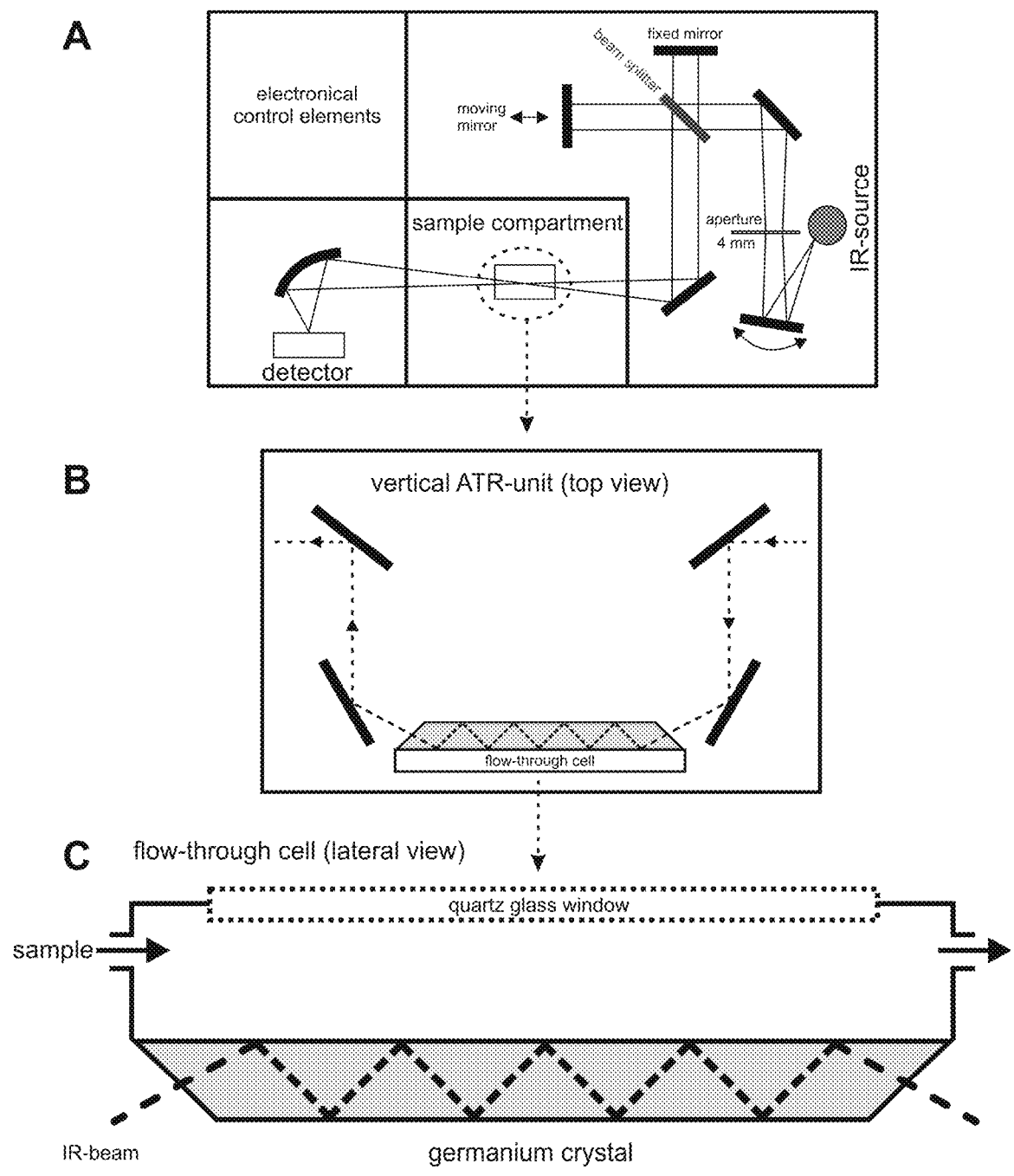
FIG. 1: Schematic view of the sensoric device in the sample chamber of an IR spectrometer (A), detailed view on the sample chamber (B), and schematics of the flow through cuvette (C).
Figure 2:
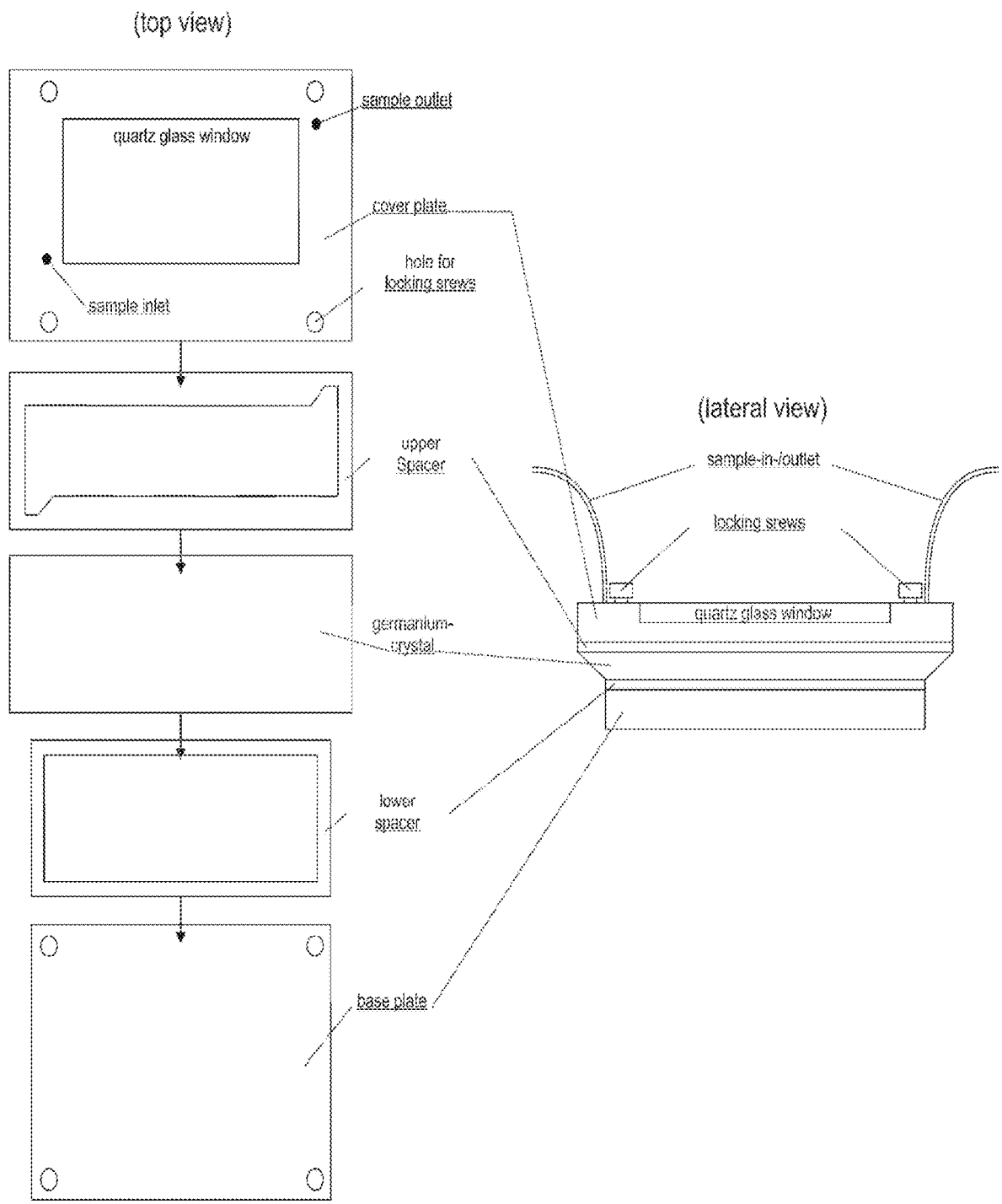
FIG. 2: Optimized flow through cuvette in detail. The device is prepared for a parallel analysis with alternative optical technique via a quartz window in the cover. Gasket elements, Inlet, and outlet ports were optimized regarding stability and flow.

The invention is based on direct and intimate immobilization of receptors for the macromolecular substance to be analysed, i.e. antibodies on a germanium surface via silane or thiol chemistry with an optimized, simplified protocol. To analyze the liquid (e.g. blood or csf), it is fed to the sensor in a flow system. The macromolecular substance is immobilized by the antibody on the functionalized sensor surface.

The optical sensor element of aspects (1) and (1') of the invention is particularly suitable for infrared analysis and optionally further for the parallel analysis by another optical method including detection of fluorescence at different wavelengths.

Furthermore, the sensor element is suitable for optical analysis of macromolecular substances including peptides and proteins, but also nucleotide-containing polymers such as DNA and RNA.

In a preferred embodiment of the optical sensor element of the invention the internal reflection element is a germanium crystal having a trapezoid or parallelogram shape, fiber or rod shaped geometry. It is preferred that the germanium crystal is a germanium monocrystal, while a trapezoid cut germanium monocrystal is particularly preferred.

It is further preferred that the germanium crystal allows for more than one passages of the infrared light through the reflection element, particularly preferred are more than five passages. For allowing the contact with the candidate biomarker protein in such multiple passages, the receptor for the biomarker protein is grafted to the appropriate number of surfaces of said internal germanium reflection element.

The silane and thiol linkers that are utilized for coupling the receptor and hence, the macromolecule to the internal germanium reflection element include homogenous silane and thiol linkers, mixtures of silane linkers and mixtures of thiol linkers. For allowing a tight and intimate linkage of the receptor/macromolecule short chained linkers, preferably linkers having a chain length of not more than 20 atoms or not more than 15 atoms, are utilized.

Such short chained linkers include silane linkers have one of the following formulas:

$$X_3Si\text{—}(CH_2)_n\text{—}Y\text{—}(CH_2)_{n'}\text{—}Z,$$

$$X_2R^1Si\text{—}(CH_2)_n\text{—}Y\text{—}(CH_2)_{n'}\text{—}Z \text{ or}$$

$$X(R^1)_2Si\text{—}(CH_2)_n\text{—}Y\text{—}(CH_2)_{n'}\text{—}Z,$$

and the thiol linkers have the following formula:

$$HS\text{—}(CH_2)_n\text{—}Y\text{—}(CH_2)_{n'}\text{—}Z,$$

wherein X at each occurrence is independently selected from halogen and $C_{1-6}$ alkoxy, n is an integers of 1 to 10, n' is an integer of 1 to 5; $R^1$ at each occurrence is independently selected from $C_{1-6}$ alkyl, Y is selected from a chemical bond, —O—, —CO—, —SO_2—, —NR^2—, —S—, —SS—, —NR^2CO—, —CONR^2—, —NR^2SO_2— and —SO_2NR^2— (wherein $R^2$ is H or $C_{1-6}$ alkyl), and Z is an amine-reactive group including —CO_2H, —SO_3H and ester derivatives thereof.

The halogen within the present invention includes a fluorine, chlorine, bromine and iodine atom. $C_{1-6}$ alkyl and $C_{1-6}$ alkoxy includes straight, branched or cyclic alkyl or alkoxy groups having 1 to 6 carbon atoms that may be saturated or unsaturated. In case of cyclic alkyl and alkoxy groups, this refers to those having 3 to 6 carbon atoms. Suitable $C_{1-6}$ alkyl and $C_{1-6}$ alkoxy groups include, among others, methyl and methoxy, ethyl and ethoxy, n-propyl and n-propoxy, iso-propyl and iso-propoxy, cyclopropyl and cyclopropoxy, n-butyl and n-butoxy, tert-butyl and tert-butoxy, cyclobutyl and cyclobutoxy, n-pentyl and n-pentoxy, cyclopentyl and cyclopentoxy, n-hexyl and n-hexoxy, cyclohexyl and cyclohexoxy, and so on. The amine-reactive group Z includes all types of functional groups that are reactive with a free amino group. Among those, —CO_2H, —SO_3H and ester derivatives thereof (including active esters) are particularly preferred.

The —(CH_2)_n— and —(CH_2)_{n'}— structural elements in the above formulas may also contain one or more double and/or triple bonds and may be substituted with one or more halogen atoms such as fluorine.

In a preferred embodiment of the invention, the optical sensor element is obtainable by silanization and in the linkers X is independently selected from $C_{1-6}$ alkoxy groups, preferably from methoxy and ethoxy groups, Y is —NHCO—, Z is —CO_2H or an ester derivative thereof, and n is an integer of 1 to 5 and n' is an integer of 1 to 3, preferably n is 3 and n' is 2.

In another embodiment, the optical sensor element is obtainable by thiolation and in the linkers Y is a chemical bond, Z is —CO_2H or an ester derivative thereof, and n is an integer of 1 to 8 and n' is an integer of 1 to 5, preferably n is 8 and n' is 4. Particularly preferred is a 12-mercaptododecanoic acid NHS ester.

In another preferred embodiment of the optical sensor element at least one receptor for the macromolecular substance is a specific antibody. Furthermore it is preferred that the macromolecular substance is a protein that is characteristic for a protein misfolding disease such as, but not limited to, Alzheimer's disease (Aß peptides and tau protein), Parkinson's disease ((alpha)-synuclein), Creutzfeldt-Jakob disease (prion protein), or chorea Huntington (huntingtin protein), preferably the macromolecule substance is an amyloidogenic peptide or a (poly-) peptide of health-status dependent, characteristic secondary structure composition.

The blocking substance not cross-reacting with the candidate biomarker protein includes casein, ethanolamine, L-lysine, polyethylene glycols, albumins, and derivatives thereof, and preferably is casein.

When the candidate biomarker protein is Aß peptide, the antibody is an antibody specifically binding to the central epitope of the amyloid-beta peptide, such as antibody A8978 (Sigma Aldrich) and when the candidate biomarker protein is alpha-synuclein, the antibody is an antibody specifically binding to the alpha-synuclein peptide without conformational specificity, such as antibody 4B12 (Covance, BioLegend Inc.) or S5566 (Sigma Aldrich).

The device of aspect (2) of the invention has the sensor element of aspects (1) or (1') of the invention incorporated in a suitable IR cell (chamber). It may further include a light (IR) emitting element, a light (IR) detecting element and a data processing unit. For parallel detection by an additional optical method the device may further include light source and detector element for such additional optical method such as light source and detector elements for UV/Vis-fluorescence, at different wavelengths.

In the method of aspects (3) and (3') of the invention, the oxidization is performed by treatment with $H_2O_2$/oxalic acid. Further, in the method the silanization with the short silane linkers is preferably performed with a silane derivative having the following formulas:

$$X_3Si\text{—}(CH_2)_n\text{—}(CH_2)_{n'}\text{—}Y,$$

$$X_2(R^1)Si\text{—}(CH_2)_n\text{—}(CH_2)_{n'}\text{—}Y \text{ or}$$

$$X(R)(R^2)Si\text{—}(CH_2)_n\text{—}(CH_2)_{n'}\text{—}Y,$$

wherein the variables are as defined above. It is particularly preferred that an ester derivative of the $CO_2H$ or $SO_3H$ moiety in the definition of Y be used, which can be a simple $C_{1-6}$ alkyl ester, but can also be an activated ester such as an N-hydroxysuccinimid ester or any other activated ester derivate. It is also preferred in the method that the receptor is an antibody. It is further preferred that the blocking substance is casein.

In the method of aspects (4) and (4') of the invention, the surface activation is performed by treatment with HF (49%). Further, in the method the thiolation with the short thiol linkers is preferably performed with thiol linkers having the following formula:

$$HS\text{—}(CH_2)_n\text{—}Y\text{—}(CH_2)_{n'}\text{—}Z,$$

wherein the variables are as defined above. It is particularly preferred that an ester derivative of the $CO_2H$ or or $SO_3H$ moiety in the definition of Y be used, which can be a simple $C_{1-6}$ alkyl ester, but can also be an activated ester such as an N-hydroxysuccinimid ester or any other activated ester derivate. It is also preferred in the method that the receptor is an antibody. It is further preferred that the blocking substance is casein.

In both aspects (3)/(3') and (4)/(4') the method of the optical sensor element is built up under room temperature without aggressive chemicals. Every single step can be assessed on the basis of the IR-spectra. This validation step is essential for the specific detection and accurate secondary structure determination of the analyte.

The method of aspects (6) and (6') of the invention comprises the steps of (a) conducting, in an IR cell comprising the optical sensor element as defined herein before, a flux of potential macromolecular ligands for the receptor on the surface of said optical sensor;

(b) submitting an IR beam through said cell and obtaining an infrared spectrum therefrom; and (c) analyzing the obtained infrared spectrum to determine the secondary structure, and optionally the quantity, of the macromolecular substance.

It may further include the step (d): analyzing the obtained infrared spectrum to classify the sample with statistical methods based on the secondary structure composition of the macromolecular substance.

In a preferred embodiment the method further comprises prior to step (a): installation of said optical sensor element in the IR cell. Additionally/alternatively the method may further comprise the step (e): regenerating of the surface of the optical element by application of a solution of free ligand for the receptor.

In a further preferred embodiment the spectrum obtained in step (b) has a sufficient signal to noise ratio to resolve the amide I band. This allows that step (c) preferably comprises the analysis of the shift of the amide I band maximum of the biomarker protein to determine the secondary structure of the candidate biomarker protein; and/or In a further embodiment the step (c) of the method further comprises comparing the obtained infrared spectrum with a spectrum of the macromolecular ligand with known secondary structure and/or with known concentration.

In another embodiment, the method further comprises, parallel to the infrared analysis, detection by another optical method, including UV/Vis-fluorescence, at different wavelengths. Notably, a method is preferred that combines immuno-ATR-IR vibrational spectroscopy with parallel fluorescence spectroscopy.

The methods of aspects (6), (6') and (7) allow/are suitable for determining macromolecules in bodily fluids, notably for directly determining candidate biomarker proteins in bodily fluids of mammalian (human, animal) origin, including cerebrospinal fluid, blood or serum, without pretreatment (i.e., without a separate preceding enrichment or purification step). The method is suitable for determination of the candidate biomarker protein in a separate (in-vitro) or an online (direct determination of the body fluid on the patient) fashion. In both cases, the method may further comprise the assessment of the disease progression.

The methods of aspects (6), (6') and (7) are particularly suitable for the determination of progression of Alzheimer's disease with amyloid-beta as candidate biomarker protein, wherein a shift of the amide I band maximum of the amyloid-beta peptide from 1647 $cm^{-1}$ to 1640 cm, preferably with a threshold value of 1643 $cm^{-1}$+/−5 $cm^{-1}$, (or 1643 $cm^{-1}$+/−3 $cm^{-1}$, or 1643 $cm^{-1}$+/−1 $cm^{-1}$, or about 1643 $cm^{-1}$), is indicative for Alzheimer's disease. These methods are also particularly suitable for the determination of progression of Parkinson's disease with alpha-synuclein as candidate biomarker protein, wherein a down shift of the amide I band maximum of the alpha-synuclein peptide from 1646 $cm^{-1}$ to 1641 $cm^{-1}$, preferably with a threshold value of 1643 $cm^{-1}$+/−5 $cm^{-1}$ (or 1643 $cm^{-1}$+/−3 $cm^{-1}$, or 1643 $cm^{-1}$+/−1 $cm^{-1}$, or about 1643 $cm^{-1}$), is indicative for the progression of Parkinson's disease.

The invention of the present application provides for the specific immobilization of receptors for macromolecular substrates such as functional antibodies on the surface of an optical element in a direct and tight manner. In contrast to the above mentioned WO 02/056018 and EP-A-1806574, which disclose the chemical functionalization of the optical element with long chain silanes and carbohydrates in order to analyze the receptor immobilization, or the receptor interaction with ligands, the tight immobilization of the receptors for macromolecules such as highly specific antibody allows for the conformational analysis of a given macromolecule as a component of a complex fluid.

With the sensor of the invention the detection limit for the Aß-peptide, a prime biomarker candidate for Alzheimer's disease, was two magnitudes lower as compared to the natural concentration in csf, and about one magnitude lower as compared to the natural concentration in blood. In the course of Alzheimer's disease, the Aß peptide conformation is changed. Conventional assays only include the concentration and the ratio of Aß-peptides with various chain lengths in the csf. With the sensor of the present invention, different Aß-conformations can be detected in real-time, and the measured absorbance presents an average signal of the present secondary structures. For Alzheimer patients, significant and specific changes in the conformational sensitive spectral region compared to control patients could be identified. Thereby, the sensitivity and practicability of the technique was shown.

Electromagnetic radiation has to be coupled into the sensor element of the invention. The usable wavelength comprises Ultraviolet to Terahertz. For prototype development, the medium infrared (MIR) region was utilized. The antibody-bound substance absorbs radiation at specific wavelengths, generating an absorbance spectrum. The intensity of the absorbance signals allows for the quantitative interpretation of the substance concentration. The absorbance wavelength enables the direct, qualitative interpretation of e.g. secondary structure in case of proteins.

In addition, the sensor element of the invention is designed for a parallel detection of at least two wavelength ranges with at least two distinct, but simultaneously applied spectroscopic methods, e.g. infrared absorbance and fluorescence measurements of the analyte.

The overall process can be largely automated. Therefore, the device and method of the invention is also operable for non-scientific personnel. The coupling of the method with classifying statistics for diagnostic purposes is also contemplated.

With the established sensor technique, defined substances can be analysed qualitatively and quantitatively directly within complex solutions, if antibodies for the desired substance are available. Therefore, a direct secondary structure analysis of proteins in untreated bodily fluids has become accessible. The specificity of the sensor is based on the specificity of the antibody. For basic research, the invention in particular enables the structural analyzes of proteins from solutions of low concentration.

By applying a bioinformatical classifier, several states of the attached substance can be differentiated automatically. The sensitivity and specificity of the discrimination has to be validated for each case.

The sensor opens the new field to search for new biomarkers with conformational classification. The use of our invention in clinical applications is in particular relevant, because bodily fluids can be analyzed directly after extraction. Only the predefined component is detected, and both the amount as well as its structure is analysed for diagnostic information.

A particular example is a neurodegenerative disease like Alzheimer's, which exhibits altered amounts and structures of the so far identified biomarker candidate molecules Aß and tau in the csf. With the invention of the present application, both parameters are detected simultaneously.

Figure 8:
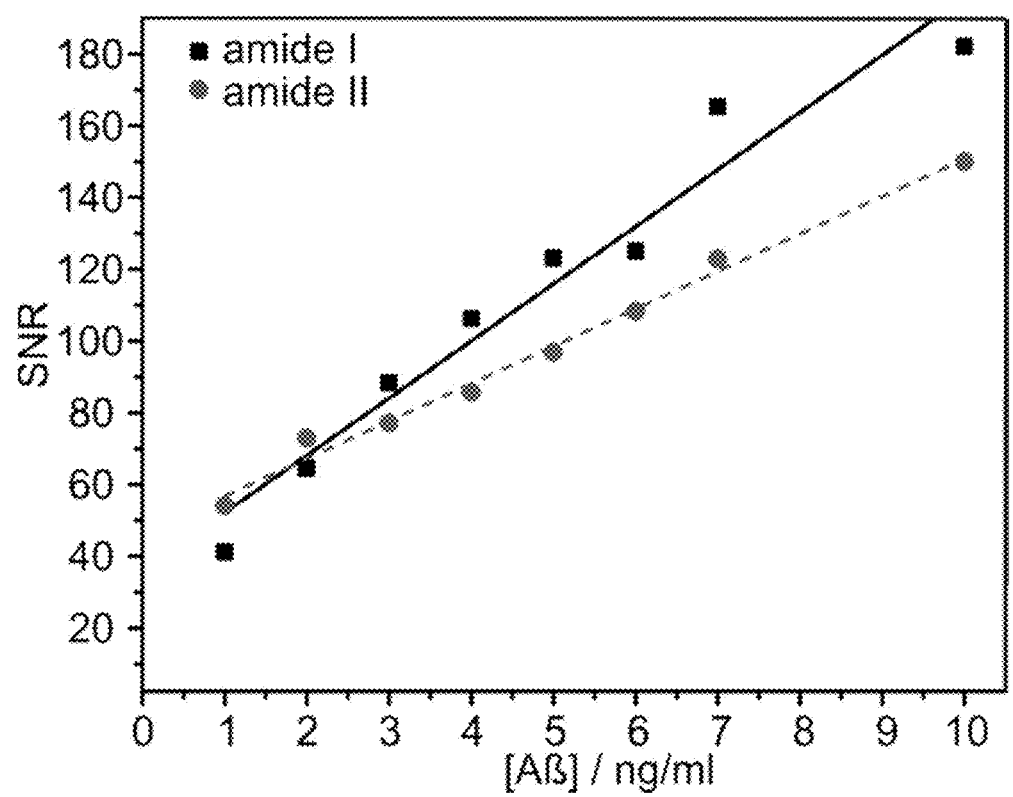
FIG. 8: Signal to noise (S/N) ratio of amide I (black squares) and amide II bands (grey circles) of synthetic Aß peptides.
Figure 16:
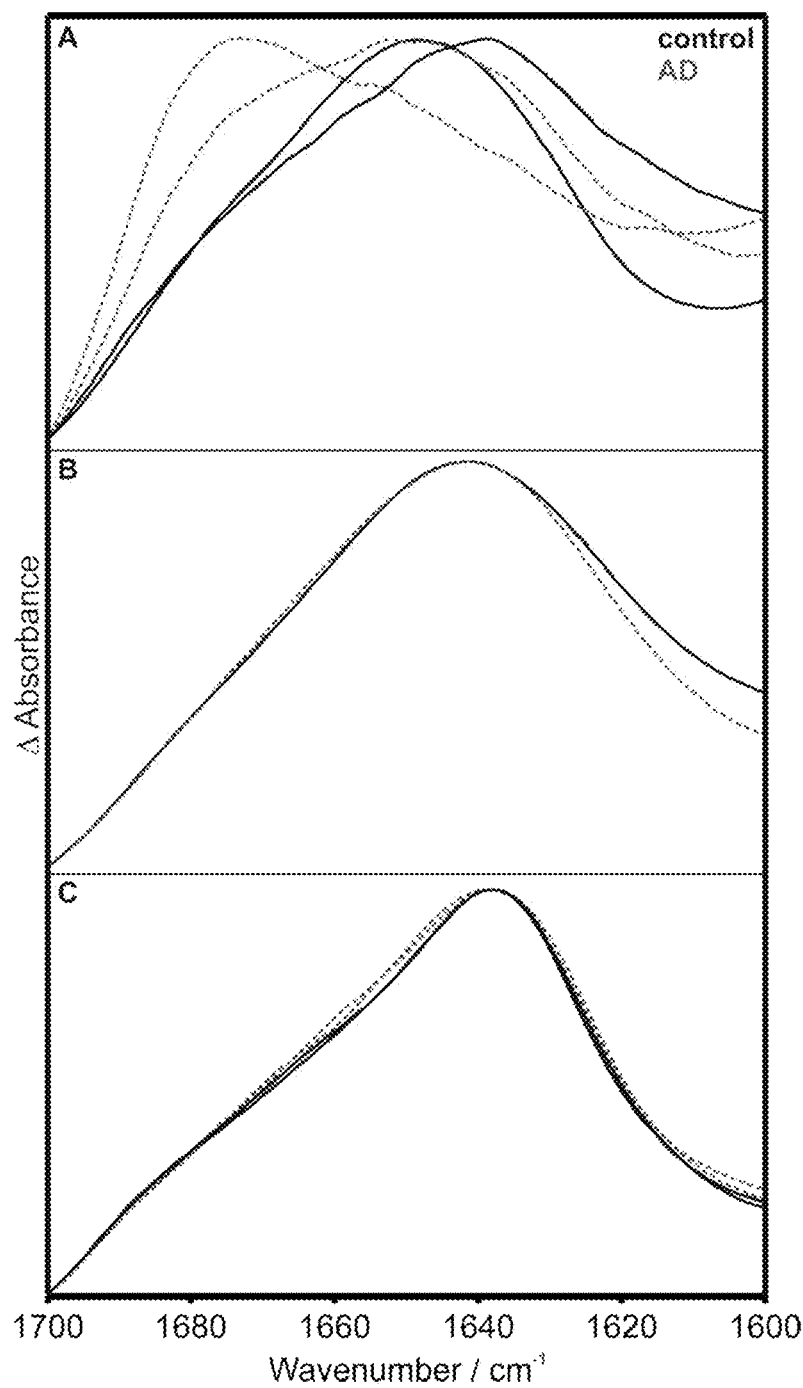
FIG. 16: Amide I bands obtained with different antibodies on a blocked sensor from the Aß fraction in CSF of control (solid, black) and AD patients (dashed, grey). 1E8 recognized an N-terminal epitope (A). KW1 captured oligomeric Aß peptides (B). B10 selected fibrils (C).

The invention provides for the secondary structure analysis of a protein amide I band of a specific protein within a complex fluid. The secondary structure is used as biomarker for the disease state. The structural sensitive frequency of the amide I in presence of the corresponding biomarker below a here defined threshold indicate the disease state. The threshold is described in FIGS. 9, 10 and 11 for the Aß peptide and in FIG. 16 for alpha-synuclein. The following detailed discussion is focussed on Aß peptide for Alzheimer and alpha-synuclein for Parkinson. This threshold is the novel finding. In order to determine the threshold, an experimental setup which provides sufficient signal to noise ratio of the amide I band in presence of the body-fluid was invented. It is important to measure the secondary structure of the biomarker in the presence of the body-fluid, because it is very sensitive to the measuring conditions. For example the Aß secondary structure varies between alpha helix and random coil depending on the measuring conditions. As example in the application the Aß peptide is used. An excellent S/N of the amide I band at analyte concentrations below physiological level (FIG. 8) was obtained. Aß peptides are concentrated at approximately 10-15 ng/ml in human cerebro spinal fluid (CSF). The demonstrated detection limit undercuts this value at least one order of magnitude.

Figure 11:
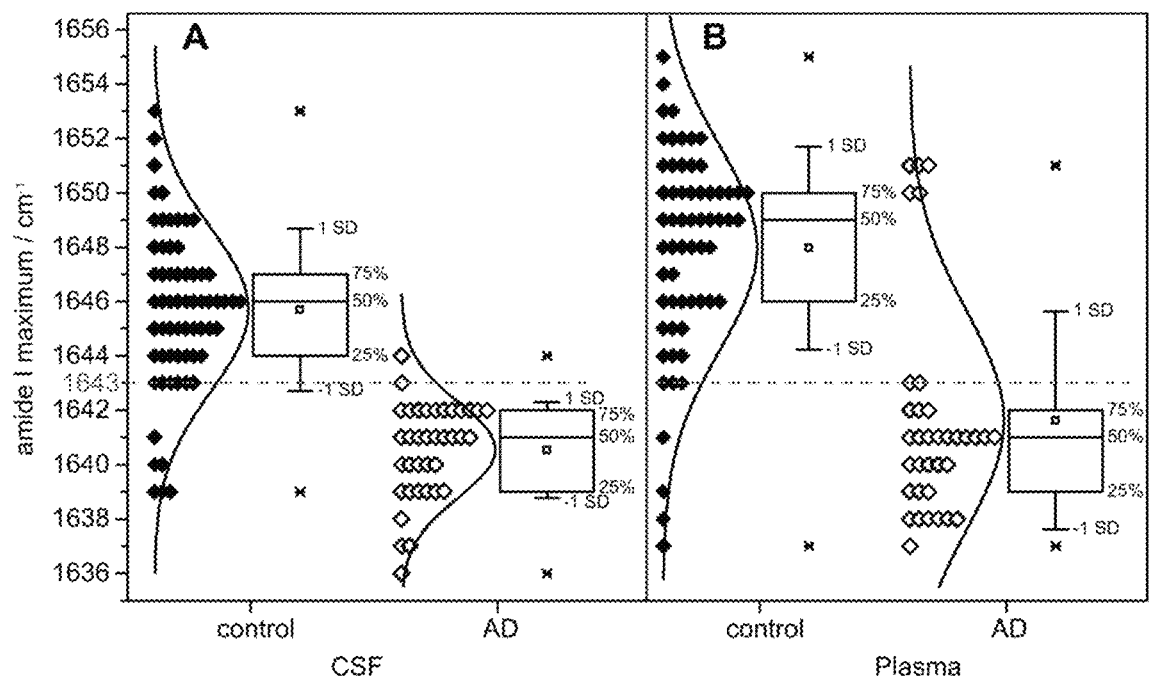
FIG. 11: Distribution of the amide I band maximum positions recorded of CSF (A) and blood plasma samples (B). Solid diamonds depict control patient samples, empty diamonds AD cases. Gaussian normal distributions well approximated the displayed histogram data. 25/50/75% quantiles are displayed in box-plots. These further indicate the average band position (square), ±standard deviation (SD, whiskers), and observed minimum/maximum values (x). A dashed line indicates the discriminative threshold position of 1643 cm$^{-1}$.

The intended protein is detected, as shown with the example Aß peptide: capture of the synthetic Aß peptide from defined, buffered solutions and from complex, conditioned cell culture medium were confirmed by the optional control analysis fluorescence (FIG. 11).

Based on the results of Examples 2 and 3, a threshold classifier with a value of 1638-1648 $cm^{-1}$ is a characteristic of the invention.

The preferred optical material of the invention is germanium. It is found that a so-called "BiaATR"-setup with only one single reflection geometry is of insufficient signal quality for the secondary structure analysis of Aß peptides at physiological concentrations. Even if Aß peptides were provided in >5 fold excess in a pure and deuterated solution, a secondary structure analysis could not be performed on the low S/N spectra achieved [Kleiren et al. Spectroscopy 2010]. Therefore, the threshold as marker for the disease cannot be determined by this approach. A preferred embodiment of the invention features a multi-reflection crystal IRE of trapezoid shape. A parallelogram shape would be closely related and similarly possible. It appears crucial to exploit at least 5 internal reflections at the functionalised surface to achieve sufficient signal to noise ratio in order to determine the threshold.

A blocking step of the antibody-saturated surface is crucial for the intended amide I band analysis of the analyte. A detergent-free solution of a globular protein, unreactive with the analyte, but reactive with the silane or thiol linker, is used for chemical quenching/blocking of unspecific binding sites of the sensor element (see Examples 5 and 6).

The finding that a non-crossreacting blocking substance such as casein is required for conformational analysis, notably amide I band analysis is important for the present invention. An immunological blocking standard, albumin, is unsuitable for the specific Aß peptide detection (see Example 7).

In immunological protocols, often dry milk powder is applied in buffered solutions. A buffered dry-milk solution is inapplicable for Aß detection because it contains albumin. Detergents are not necessary for the sensor system. All examples have been performed with detergent-free solutions. Complications with the invention are not expected with common low concentrations of detergents as used in immunological protocols.

For the analysis of the Aß peptide secondary structure in a sample, the antibody has to be sensitive (specific) for a central peptide epitope, but insensitive to the epitope structure the peptide (see Example 8).

The methods of aspects (6) and (7) of the invention are applicable for a variety of conformational diseases, also known as protein misfolding diseases, or proteopathies, which are caused by the misfolding of the following peptides/proteins: Amyloid-beta (Aß) peptides and tau protein (Alzheimer's Disease (AD)); alpha-synuclein (Parkinson's Disease (PD)), prion protein (Creutzfeldt-Jakob disease (CJD), Bovine spongiform encephalopathy (BSE) commonly known as mad cow disease), huntingtin protein (chorea Huntington).

Specifically shown is the use for analysis of Aß (Examples 1 to 8) and alpha-synuclein (Example 9).

The invention is further explained in the following non-limiting examples.

EXAMPLES

Material and Methods

Figure 3:
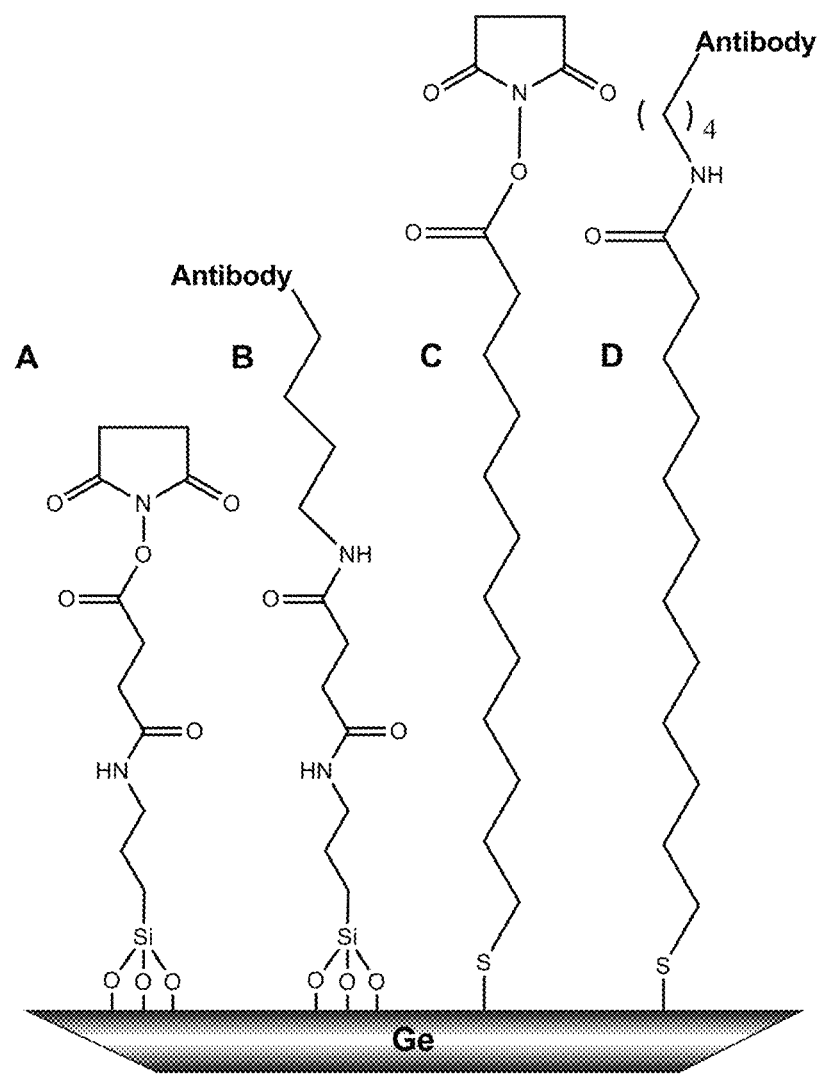
FIG. 3: Short chain triethoxysilane (N-(4,4,4-Triethoxysilanebutyl)succinamic Acid 2,5-Dioxopyrrolidin-1-yl Ester) was covalently attached to germanium (A). The succinimidyl ester reacts with free amines of e.g. proteinogenic lysines, which leads to a stable attachment of the desired protein, e.g. an antibody, of which the attached lysine side chain is shown (B). As alternative linker, 12-mercaptododecanoic acid NHS ester was also covalently attached to germanium (C). The NHS ester reacts with free amines of e.g. proteinogenic lysines, also forming a covalent bond (D).

The invention can be used directly with an IR-spectrometer equipped with the commercially available sample compartment "GS 11000-25 Reflection Variable Incidence Angle ATR" of Specac (Specac Ltd., Slough, England) (FIG. 1 A, optical path FIG. 1 B). The optical element, a germanium ATR-crystal (52×20×2 mm, Korth Kristalle GmbH, Altenholz (Kiel), Germany), was enclosed in an optimized bracket (FIG. 1 B, 2). Subsequently specified chemical modifications of the crystal surface generated the specific sensor-property (FIG. 3). If not mentioned otherwise, all chemicals were purchased from Sigma-Aldrich (Munich, Germany). Buffers and water were degassed in the ultrasonic bath.

Sample Set:

The feasibility study first included 23 patients, 9 patients with a best possible confirmed Alzheimer diagnosis and 14 non-neurodegenerative controls. With continued recruiting, analyses were performed with csf samples of 37 AD and 63 control patients, and blood plasma samples of 35 AD and 61 control patients. The diagnosis of the patients is based on psychological reports, MRT-imaging data, results of csf and blood analysis, and psychometric test diagnostics. Based on availability, PET (positron emission tomography) or SPECT (single photon emission computed tomography) findings were considered. Additional reports results from course observations involving close relatives.

Sampling and Pretreatment:

Csf was drawn by lumbal puncture and aliquoted at the university hospital Essen, snap-frozen in liquid nitrogen, shipped and stored at −80° C. Samples were not pretreated before the measurement, only thawed at 37° C. for 30 seconds and kept on ice until used.

Phosphate Bufferd Saline (PBS-Buffer):

137 mM sodium chloride (NaCl), 2.7 mM potassium chloride (KCl), 12 mM total-phosphate (in the form of $Na_2HPO_4$ and $NaH_2PO_4$), pH 7.4.

Reaction-Phosphate Buffer:

50 mM $Na_2HPO_4/NaH_2PO_4$, pH 8.0.

Casein Blocking-Solution:

200 mM sodium hydroxid (NaOH), 1% (w/v) casein from bovine milk (powder), pH adjusted with $H_3PO_4$ to 7.4.

Silanization-Solution:

The silane used (N-(4,4,4-triethoxysilanebutyl)succinamic acid 2,5-dioxopyrrolidin-1-yl ester) was synthesized and characterized as described (J. Schartner et al., Journal of the American Chemical Society, 135(10):4079-4087 (2013)).

Antibody:

The method was tested with two antibodies as capture molecules, 1E8 (Nanotools Antikörpertechnik GmbH, Teningen, Germany) and A8978 (lot no: 061M4773 Sigma Aldrich). 1E8 attaches to the N-terminal amino acids 1-11, A8978 attaches to the amino acids 13-28 of the amyloid-beta peptides. The fluorescence detection occurred through FITC-labeled 8G7 antibody (Nanotools), which recognizes the C-terminus of $Aß_{1-42}$ peptides. In addition conformation sensitive antibodies against oligomeric states (KW1) were utilized (Morgado et al., PNAS, 109(31): 12503-12508 (2012)) and fibrillar states of Aß-peptides (B10) (G. Habicht et al., Proc. Natl. Acad. Sci. USA, 104(49):19232-19237 (2007)).

Preparation of the Sensor Surface with Silanes:

The Ge-IRE was bilaterally polished with 0.1 am grained diamond grinding suspension for 5 min (Struers A/S, Ballerup, Denmark). The crystal was incubated three times in a hydrogen peroxide/oxalic acid mixture (9:1) for 5 min, rinsed with water between every incubation step and dried with nitrogen gas. Furthermore the crystal was immediately installed with optimized silicone wavers in the flow-through-cell. The flow-rate was regulated at 1 ml/min by a peristaltic pump (IDEX Health&Science GmbH, Wertheim, Germany). The total-volume of the system amounted to 650 al.

The sensor surface was incubated with 300 μM silane solution (FIG. 3) in 2-propanol for 60 min, unspecifically linked silane was rinsed with 2-propanol for 30 min. After media change to the reaction buffer, 25 μg/ml antibody solution was flushed over the activated silane surface until saturation, monitored by the immobilization kinetics of the amide II band of the antibody. Unspecifically bound antibody was rinsed with PBS-buffer until an equilibrium of the amide II absorbance was achieved. Free reaction sites of the sensor surface were saturated with casein blocking solution followed by rinsing with PBS buffer.

Preparation of the Sensor Surface with Thiols:

The Ge-IRE was prepared identically as described for silanization. The crystal was prepared as described by (S. M. Han et al., JACS, 123(10):2422-2425 (2001)). After HF treatment, the crystal was immediately immersed into an isopropanol solution containing 1 mM 12-mercaptododecanoic acid NHS ester. The monolayer was assembled after 24 h, the crystal was dried with $N_2$-gas and immediately installed into the ATR set up. Unbound thiols were removed by washing for 30 min with isopropanol. Further preparation was identical to the silanization protocol.

Performing the Measurement:

IR-measurements were performed on a Vertex 70V spectrometer (Bruker Optics GmbH, Ettlingen, Germany) with liquid nitrogen cooled mercury-cadmium-telluride (MCT) detector. Double-sided interferograms were recorded in forward-backward interferometer movement at a 60 kHz data rate with a spectral resolution of 2 $cm^{-1}$, Blackman-Harris-3-Term-apodisation, Mertz-phase correction and 4 times zero filling. Reference spectra were recorded as an average of 1000, sample spectra of 200 interferograms. Recording reference single channel spectra of the blank sensor, sensor with 2-propanol, the silanized surface, the buffers, antibody or casein coated surface in equilibrium states enabled high sensitivity difference spectroscopy based on Lambert-Beer law ($E=-\log(I/I_0)$). The absorbance of the state change is the negative decadic logarithm of the intensity relation before and after the change. 50 al csf were added to the PBS-buffered system in a circulating flow for the secondary structure analysis of the Aß-peptide fraction. After the binding equilibrium was achieved, unbound material was rinsed with PBS-buffer from the system until no spectral changes were observed. Thus, the Aß absorbance spectrum was calculated from the difference between this state and the casein blocked, PBS rinsed sensor surface.

Pretreatment of the Spectra:

Spectral traces of atmospheric water vapor were removed by scaled subtraction of a reference spectrum. High frequency noise with a full width at half height (FWHH) of less than four wavenumbers was removed through a Fourier low pass filter. Spectra were baseline corrected as described (J. Ollesch et al., The Analyst, 138(14):4092 (2013)), and normalized to the same amide I signal intensity between 1730 and 1620 $cm^{-1}$ before classification.

Classification:

In order to reduce the dimensionality of spectral data, the position of the amide I maxima of the average spectra of both patients groups was chosen as classification relevant data points. The classification of the data resulted from a linear discriminant analysis (LDA), by matlab programming environment, version 2012a. The program intern function ('classify') was used. All calculations were done on an office PC with Intel Core2Quad CPU Q9650@3.0 GHz, 8 GB RAM (Dell Optiplex 780).

Example 1: Analysis of the Amide I Band in Aß with Silane-Coupled Linkers

Figure 4:
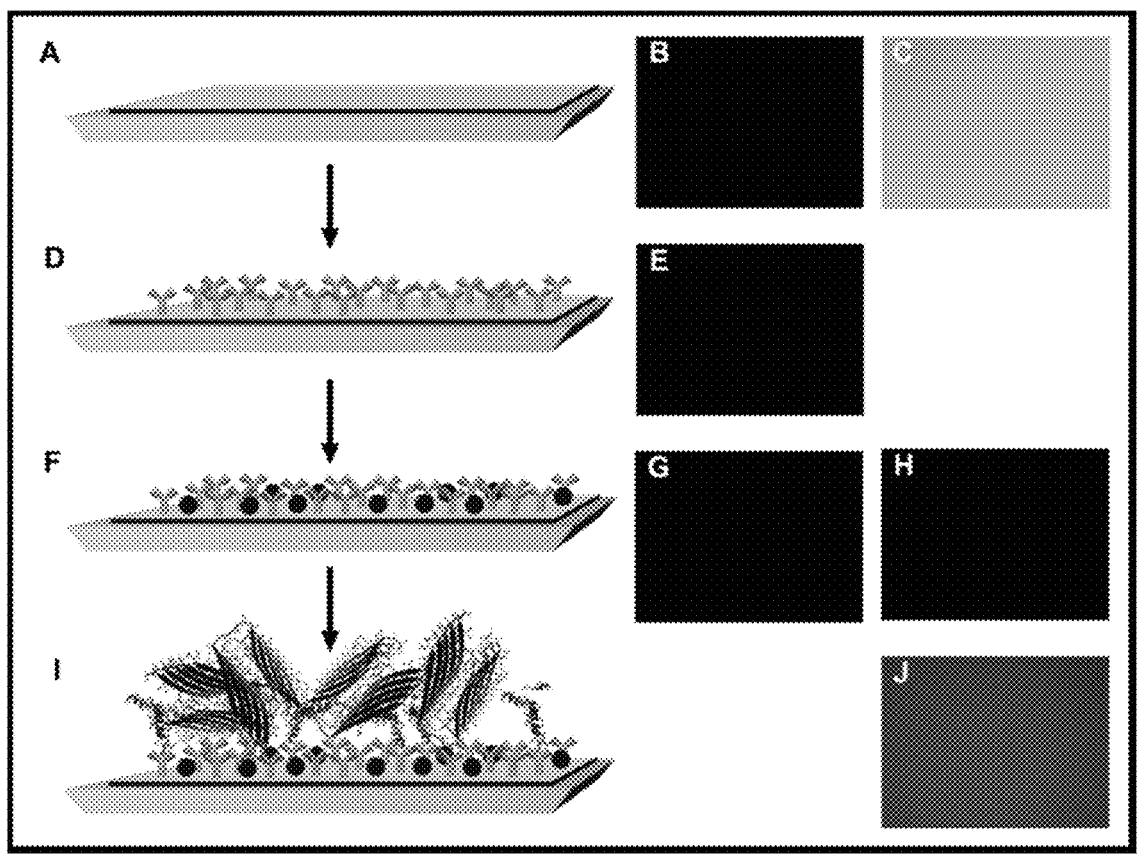
FIG. 4: Fluorescence microscopical analysis of the experiment. On reactive silane (A), no fluorescence was detected (B), but 8G7-FITC antibodies were bound (C). Binding of the detection antibody 1E8 (D) does not increase fluorescence (E). The casein blocked surface (F) does neither show fluorescence (G) nor bind detection antibody 8G7-FITC (H). Only specifically immobilized Aß-peptide (here: Aß$_{1-42}$, I) captures antibody 8G7-FITC (J).

The specific sensitivity of the established sensor setup (FIG. 1, 2) is defined by the antibody. By using fluorescence microscopy it was possible to determine fluorescence only if the FITC coupled antibody 8G7 was attached onto the surface. The control did not reveal any fluorescence (FIG. 4). The antibody 8G7-FITC was attached covalently to the amine-reactive silane surface (FIG. 3 A, B) and could not be removed by washing with buffer (FIG. 4 C). Another tested antibody 1E8 did not show any fluorescence (FIG. 4 E). After blocking open, nonspecific binding sites with casein, no further binding of the 8G7 was observed, which shows that 8G7 neither binds to casein nor to 1E8. If looking on 8G7-FITC as a protein in general, this experiment shows the silane surface being shielded from unspecific interaction with the contained proteins in the sample. Only after the incubation with the $Aß_{1-42}$ peptide, a fluorescence signal was detected from the subsequent 8G7-FITC labeled surface (FIG. 4 J), which proves the successful immobilization of Aß. Furthermore, it was shown that the designed sensor allows parallel experiments with different optical techniques.

Figure 5:
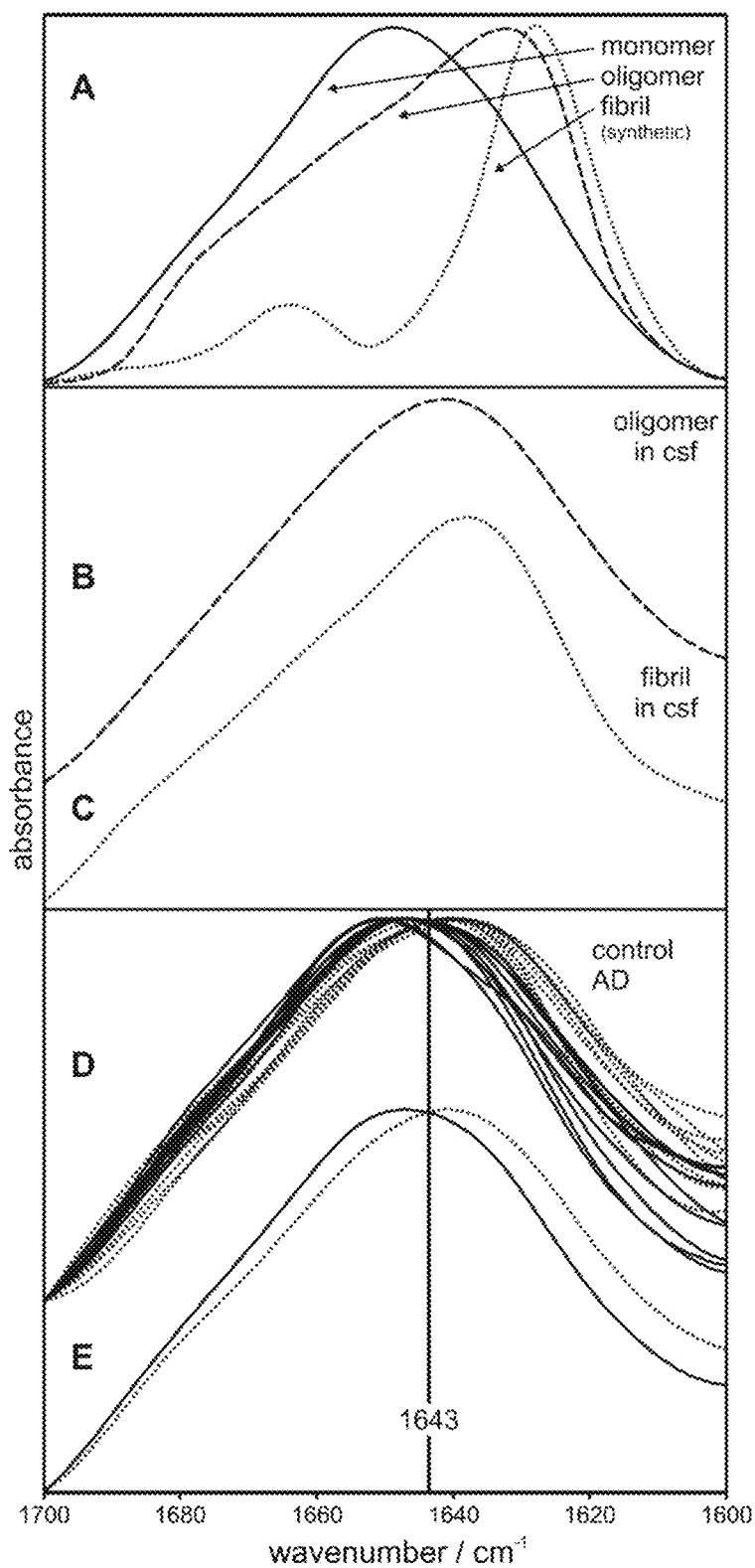
FIG. 5: The amide I marker bands of the infrared absorbance of Aß peptides, that are used for discrimination of non-neurodegenerative control patients from Alzheimer disease patients with our invention. Synthetic, isolated Aß peptides in "healthy", monomeric (solid line), "disease" oligomeric (dashed) and "disease" fibrillar conformation (dotted) (A) were captured by antibody 1E8 to the ATR surface. The secondary structure composition unambiguously differs. The amide I band of the oligomeric Aß fraction from human csf captured with antibody KW1 (B, dashed) differs from the native fibrillar fraction as captured with antibody B10 (C, dotted). Both reflect the natural conformational variety as compared to synthetic samples. The Aß fractions from unprocessed csf of 14 control (solid) and 9 Alzheimer disease patients (dotted), captured with conformationally independent antibody A8978 (D), differ less than synthetic peptides in defined conformations. Nevertheless, the separation is unique: all control amide I maxima are above 1643 cm$^{-1}$, all Alzheimer patients below (separating line). Even more pronounced, the arithmetic average of the class spectra indicates the different band positions (E).

The conformational sensitivity of the analyzed amide I band was proven with monomeric, oligomeric and fibrillized $Aß_{1-42}$ peptide (FIG. 5 A). The fibrillar and oligomer states differ strongly from non-aggregated peptide, which can be seen by the higher amount of ß-sheets. This can be revealed by a shift of the amide-I-maximum towards 1624 cm$^{-1}$ and 1630 cm$^{-1}$. The high-frequency component at 1665 cm$^{-1}$ is fibril characteristic. The oligomerized Aß-peptide is discussed as a toxic intermediate in the formation of amyloid plaques in Alzheimer patients (I. Benilova et al., Nature Neuroscience, 15(3):349-357 (2012)). Oligomers have a different ß-sheet structure compared to monomers and fibrils. A possible explanation is the higher amount of antiparallel sheets (Cerf et al., The Biochemical Journal, 421(3):415-423 (2009); Yu et al., Biochemistry, 48(9):1870-1877 (2009); Laganowsky et al., Science, 335(6073):1228-1231 (2012)) (FIG. 5 A, shoulder in the green band at about 1682 cm$^{-1}$). This implies a different amide I band for monomers and fibrils.

With the conformationally sensitive antibodies B10 (fibrils) and KW1 (oligomers), we were able to detect both corresponding Aß-peptide fractions within the same natural human csf of a control patient (FIG. 5 B, C). In comparison with a synthetic solution of isolated Aß peptides, in which only the secondary structure of the isolated peptide in defined conformation is revealed, the data from FIGS. 5 B and C presents the expected secondary structure compositions as present in the natural body fluid.

Therefore, conformationally sensitive antibodies are not suitable for the detection of disease related structural changes. These antibodies specifically detect only the desired conformation, but the important feature is the proportionate composition of monomers, oligomers and amyloid fibrils. With the conformationally independent antibody A8978, the detected amide I band resembled the structural composition of the Aß-peptide fraction quantitatively. It is likely, that this causes the high specificity of our sensor technique to discriminate patients (FIG. 5 D, E).

Figure 6:
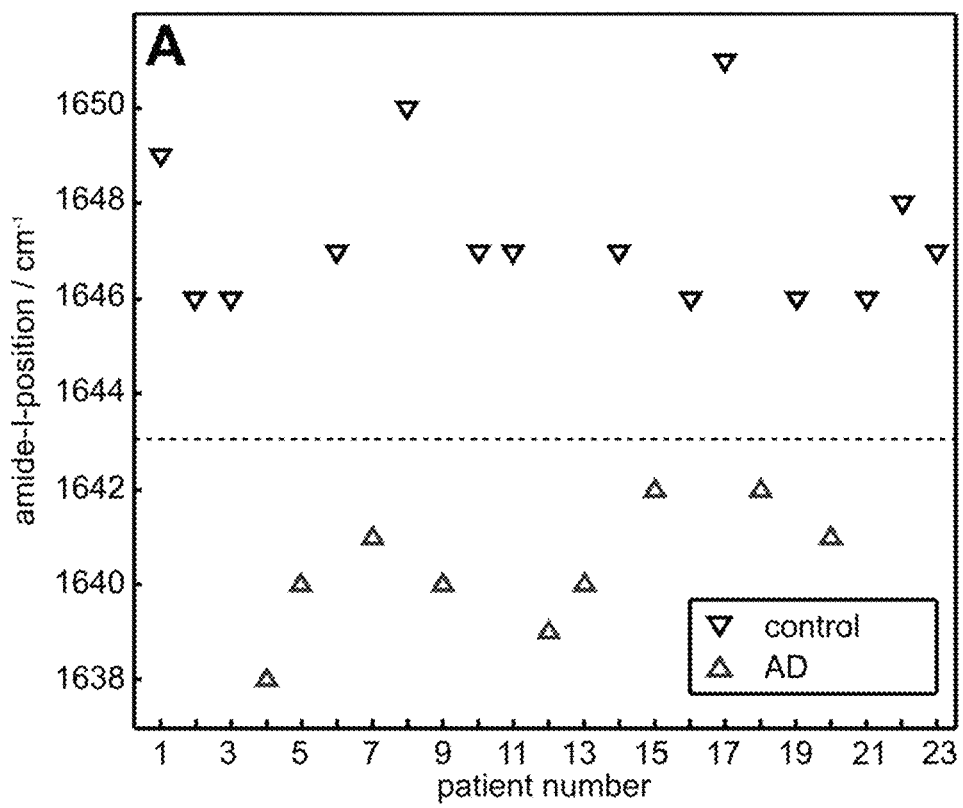
FIG. 6: The amide I band position enables a unique discrimination of control from Alzheimer disease patients (A). A classifying LDA with quadratic separation function calculated with extinction values at 1647 and 1640 cm$^{-1}$ confirmed these findings (B).
Figure 6:
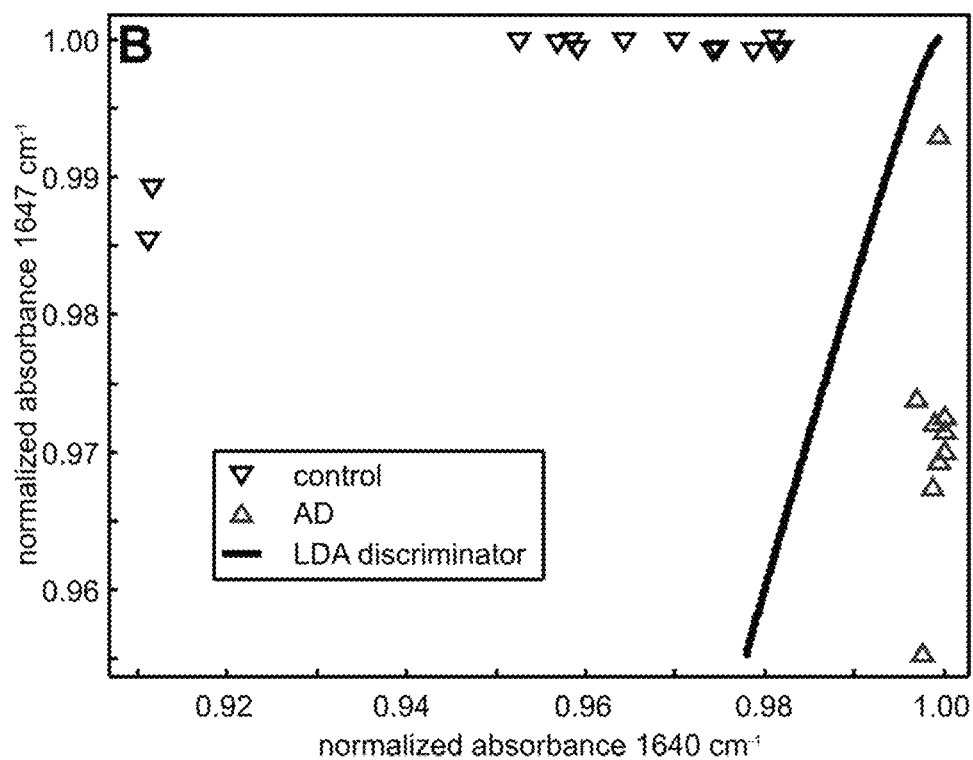

The discrimination of control—from Alzheimer patients based on the amide I maximum position is possible with 100% accuracy (FIG. 6 A).

An alternative classifier, an LDA based on the amide I intensity at 1647 and 1640 cm$^{-1}$, results in 97±6% average accuracy with 94±11% sensitivity and 100±0% specificity, based on a 1000 fold repeated Monte Carlo cross validation leaving one third of data out for classifier validation (FIG. 6 B).

Figure 7:
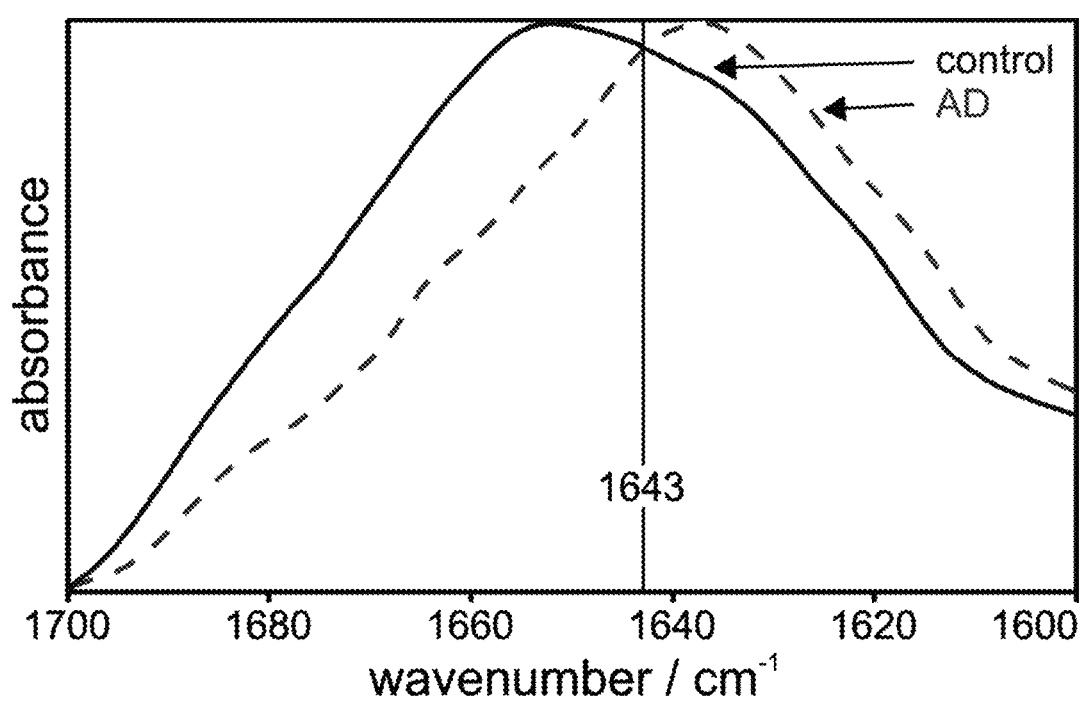
FIG. 7: The amide I band maxima of the Aß peptide fractions of EDTA stabilized blood plasma obtained from a control and an Alzheimer disease patient discriminate identically to Aß of csf (FIG. 5E). Antibody A8978 was linked via 12-mercaptododecanoic acid NHS ester to the Ge-IRE.

With the antibody linked covalently via 12-mercaptododecanoic acid NHS ester as thiol linker on the germanium IRE (FIG. 3 C, D), an identical discrimination of AD from control patients based on the secondary structure of the EDTA stabilized blood plasma Aß-peptide fraction was achieved (FIG. 7).

Example 2: Analysis of Aß Peptide Structure in CSF of Alzheimer's Disease (AD) Patients and a Control Group, Extended Data Set of 37 AD and 63 Controls The original exemplary analysis of 20 samples was extended to 100 patients. The average conformation of Aß peptides, as present in CSF, exhibited a higher amide I band frequency in the control than the AD group (FIG. 9A). This indicated a predominant alpha-helical fold in the control, whereas the AD group already exhibits an enriched beta-sheet component. Using the amide I band frequency as indicator, 1643 cm$^{-1}$ so far represents the optimum threshold for discrimination of the classes with an accuracy of 92%, a sensitivity of 95%, and specificity of 90%. The according receiver operator characteristic (ROC) curve depicts an area under curve (AUC) of 0.93 (FIG. 9B).

Example 3: Application for the Analysis of Aß Peptide Structure in EDTA-Stabilized Blood Plasma of 35 AD and 61 Control Patients As with CSF, the average conformation of Aß peptides detected in blood plasma exhibited a higher amide I band frequency in the control than the AD group (FIG. 10A). This indicated the same disease influence on the blood-borne Aß peptide fraction. Again, 1643 cm$^{-1}$ represents the optimum frequency threshold for discrimination of the classes with an accuracy of 89%, a sensitivity of 80%, and specificity of 93%. The according ROC curve depicts an AUC of 0.85 (FIG. 10B).

In Examples 2 and 3 CSF samples of 37 AD and 63 control patients, and blood plasma samples of 35 AD and 61 control patients were analysed.

The according histogram and box plots confirmed the findings with well differentiated maxima of the distributions (FIG. 11). All classes were well approximated with a Gaussian normal distribution. The average band positions of the CSF control and AD classes did not overlap with ±1 standard deviation. A two-sided t-test indicated a significant class difference with p<0.001 for both sample groups, CSF and plasma.

The maximum amide I band positions of the Aß peptide fractions were well separable by a simple classifying threshold: band maxima below 1643 cm$^{-1}$ were assigned to the AD class, equal or above 1643 cm$^{-1}$ as control patients. This threshold represents the classifier with optimum accuracy of 92% for CSF, and 89% for blood plasma samples.

Based on t-test statistics at 99.9% confidence level, a generalized classifying threshold is expectable in a range of 1638-1648 cm$^{-1}$.

Figure 12:
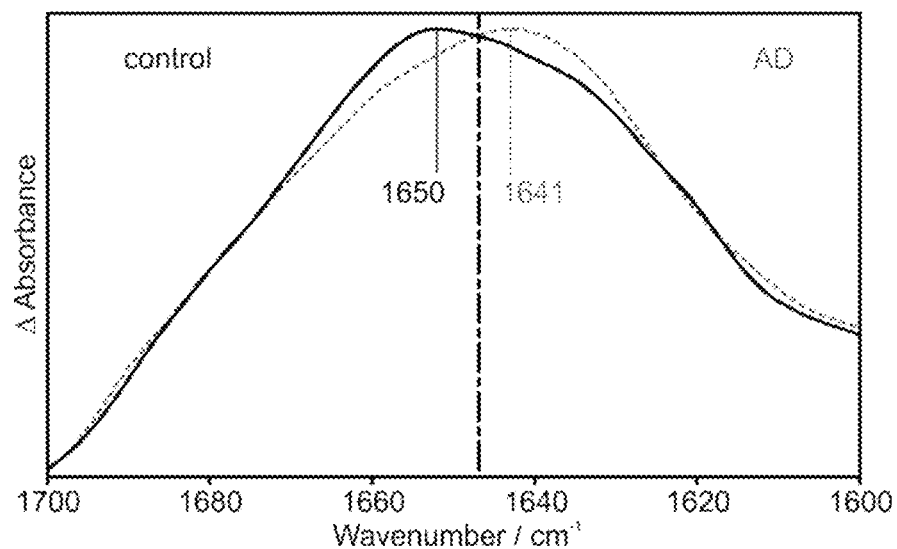
FIG. 12: The amide I band as detected from CSF of two patients with the sensor prepared with thiol linkers instead of silane linkers of the mAB A8978 exhibits identical band features for disease class separation (dash-dotted line).

Example 4: Aß Peptide Captured from AD and Control Patient CSF Via a Thiol Linker The germanium IRE of the setup was polished, cleaned with acetone, incubated in HF (10 min 40% at room temperature), washed with distilled water, blown dry in $N_2$, modified over night with a thiol linker (12-mercapto-undecanoic-acid-NHS-ester, FIG. 3C, 3D), buffer-rinsed, functionalized with antibody A8978, and desensitised with casein. The Aß fraction of CSF samples of one AD and one control patient exhibited identical discriminative features as detected with silane linkers, the classifying threshold of 1643 cm$^{-1}$ proved valid (FIG. 12).

Example 5: An Unblocked Sensor Element is Receptive for Aß Peptides and Two Selected Blood/CSF Components Three sensor elements were polished, silanized, and saturated with 1E8 antibody against Aß peptides. Two were used after rinsing out unspecifically bound antibody molecules, one was blocked with casein solution and rinsed. On one unblocked sensor, alpha-synuclein was incubated at 20 ng/ml concentration, rinsed, and Aß$_{1-40}$ peptide was incubated at 15 ng/ml concentration, and rinsed. The other unblocked sensor was incubated with albumin at 25 µg/ml concentration, rinsed, and Aß$_{1-40}$ peptide was incubated at 15 ng/ml concentration, and rinsed. The sensor elements were receptive for alpha-synuclein and albumin at concentrations which are expectable in bodily fluids (FIG. 13A).

The binding was unspecific, because the binding sites for Aß peptides were free in either case, a regular Aß peptide signal was recorded.

Figure 13:
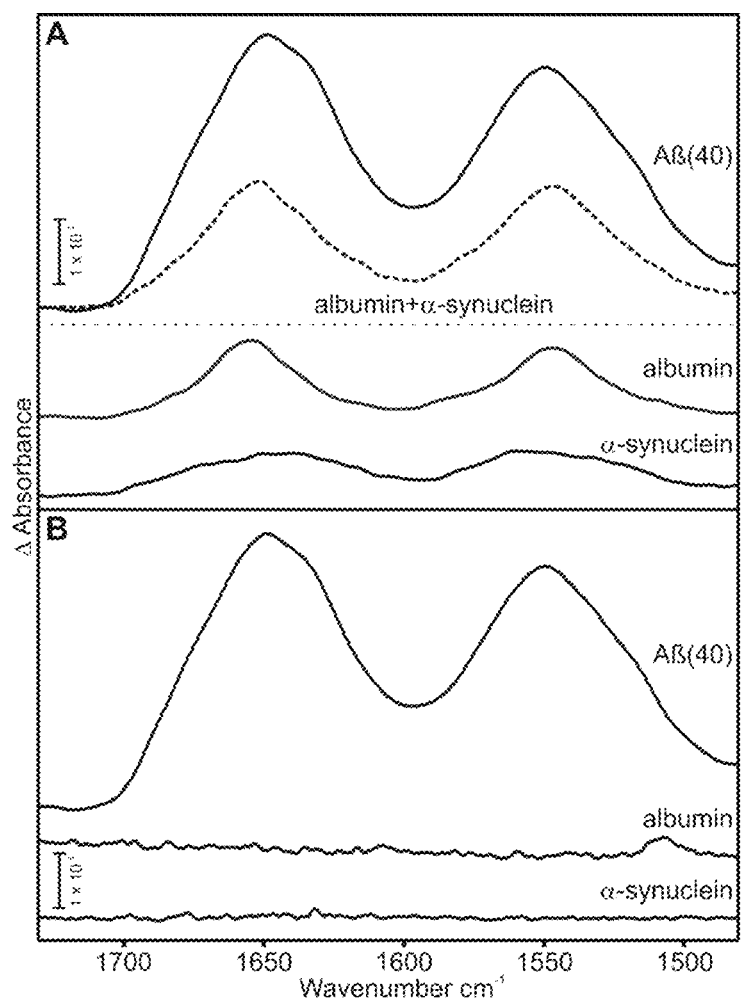
FIG. 13: (A) Unblocked sensors readily bound alpha-synuclein or albumin from pure samples (separate sensor elements) and remained receptive for Aß peptides from a pure solution in serial application of these proteins (dotted: combined signal of albumin and alpha synuclein). (B) A blocked sensor exhibited no detectable binding of alpha-synuclein and albumin. Only Aß peptides were detected after serial application.

The blocked sensor was incubated with 20 ng/ml alpha-synuclein solution and rinsed, without observable binding to the sensor surface (FIG. 13B). Consecutively, the sensor was incubated with 25 µg/ml albumin and rinsed, again without observable albumin signal. Only the incubation with 15 ng/ml Aß$_{1-40}$ peptide solution resulted in a regular signal after rinsing (FIG. 13B).

Example 6: The Sensor without Blocking Step is Inapplicable for Diagnostics

Figure 14:
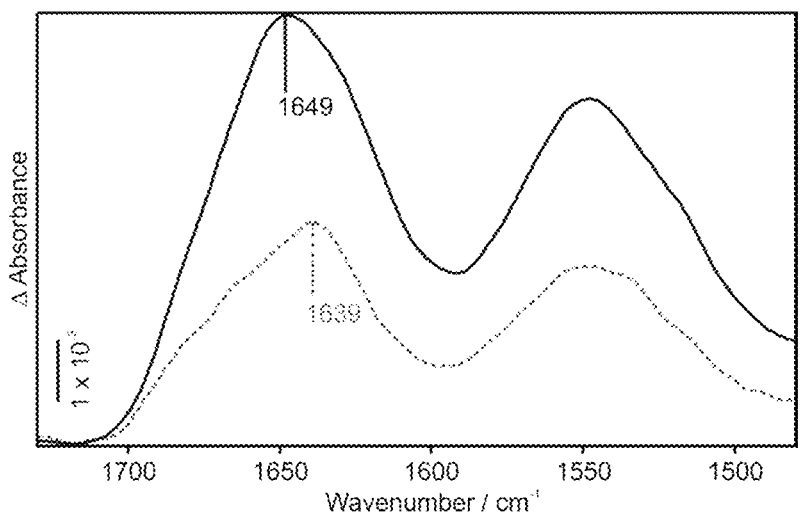
FIG. 14: Amide I and II bands obtained with a blocked (dashed, grey) and an unblocked sensor element (solid, black) after incubation with CSF of a confirmed AD patient.

Two sensor elements were prepared: one with, and one without casein blocking step. CSF aliquots of an AD patient were incubated on the sensors for the Aß amide I band analysis. The amide I band intensities recorded at the unblocked surface exhibited a far higher, thus more unspecific binding (FIG. 14). Without blocking, the band position no longer correlated with the disease state: the unblocked sensor readout indicated a predominant alpha helical conformation at 1649 cm$^{-1}$, whereas the blocked sensor readout indicated beta-sheet enrichment with the Aß maximum amide I frequency at 1639 cm$^{-1}$.

A higher maximum frequency is thus attributable to the unspecific detection of the predominantly helical protein background in CSF.

Example 7

Figure 15:
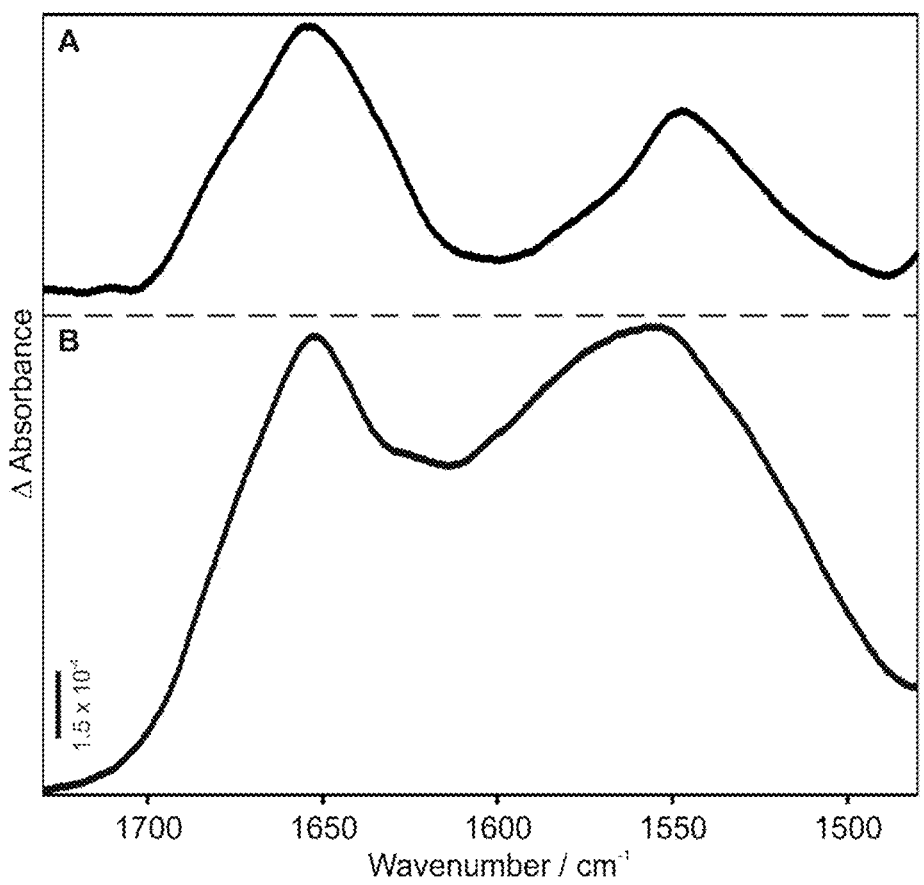
FIG. 15: Amide I and II bands obtained with the sensor after incubation with conditioned cell culture medium and consecutive rinsing. Blocking of the surface with casein resulted in the expected band pattern and intensities of mostly alpha helical Aß peptides (A). Using albumin instead of casein, an increased signal intensity and an irregular band pattern indicate overlaying spectral contributions of undesired substances (B).

With the sensor element prepared by silanisation, antibody functionalization, blocking with casein, incubation with conditioned cell culture medium, and rinsing of unspecifically bound proteins, a regular amide band pattern was observed: the amide II band was less intense than the amide I band (FIG. 15A). Fluorescence control analysis confirmed Aß peptide binding (FIG. 4)

Contrastingly, the amide band pattern recorded with another aliquot of the same sample exhibited a higher amide II intensity, when albumin instead of casein was used for blocking. The overall amide I intensity was increased by approximately 100%. Thus, albumin obviously provided additional unspecific binding sites for not further definable proteins and other substances featuring an absorbance between 1600-1500 cm$^{-1}$ (FIG. 15B).

Figure 9:
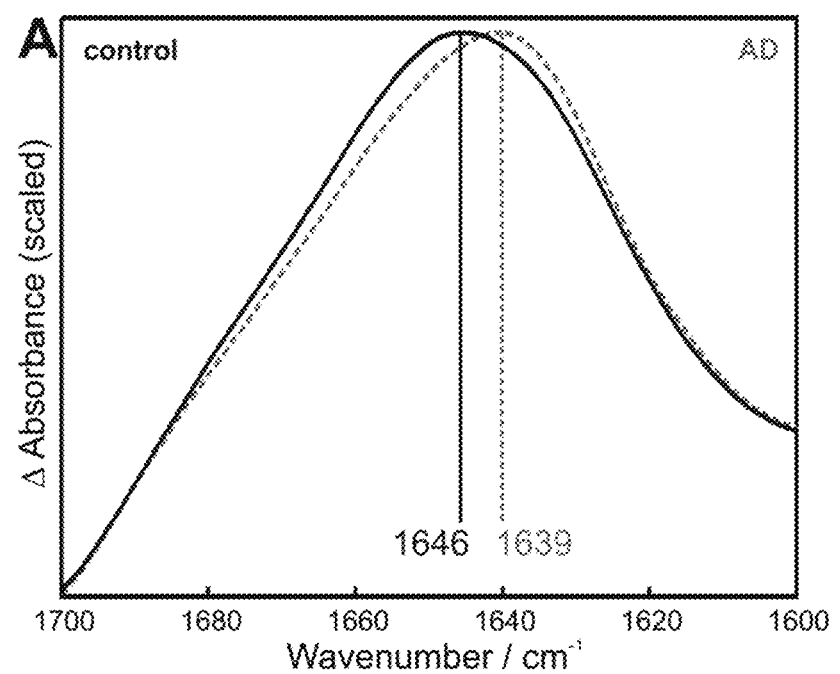
FIG. 9: The average amide I bands of 37 AD and 63 non-neurodegenerative control patients as detected from CSF (A) indicate a clear frequency downshift in AD patient samples. Using a frequency threshold as discriminator, the ROC curve indicated an AUC of 0.93 (B).
Figure 9:
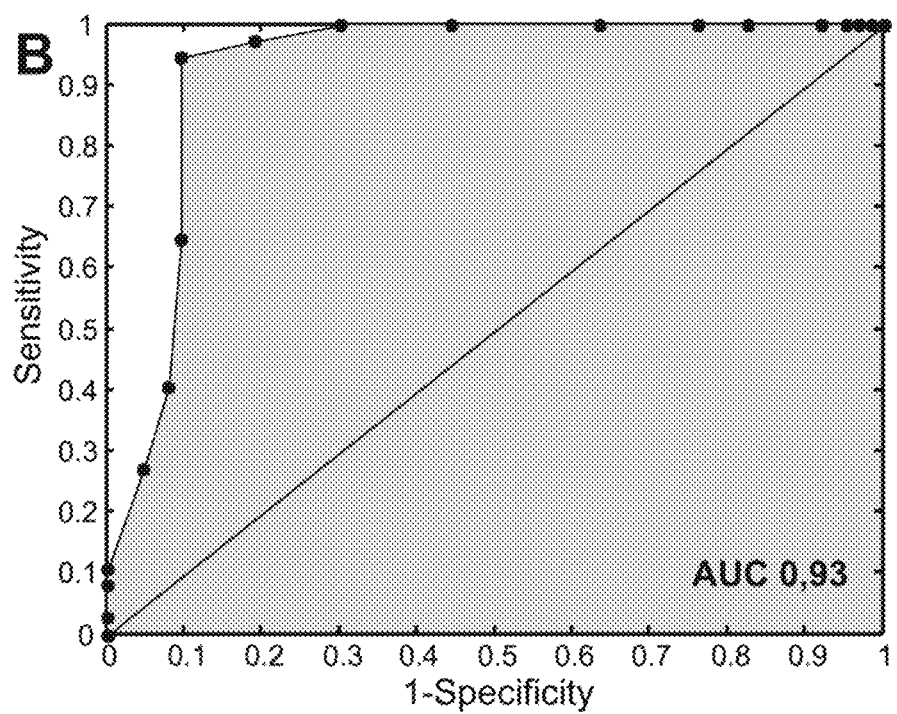
Figure 10:
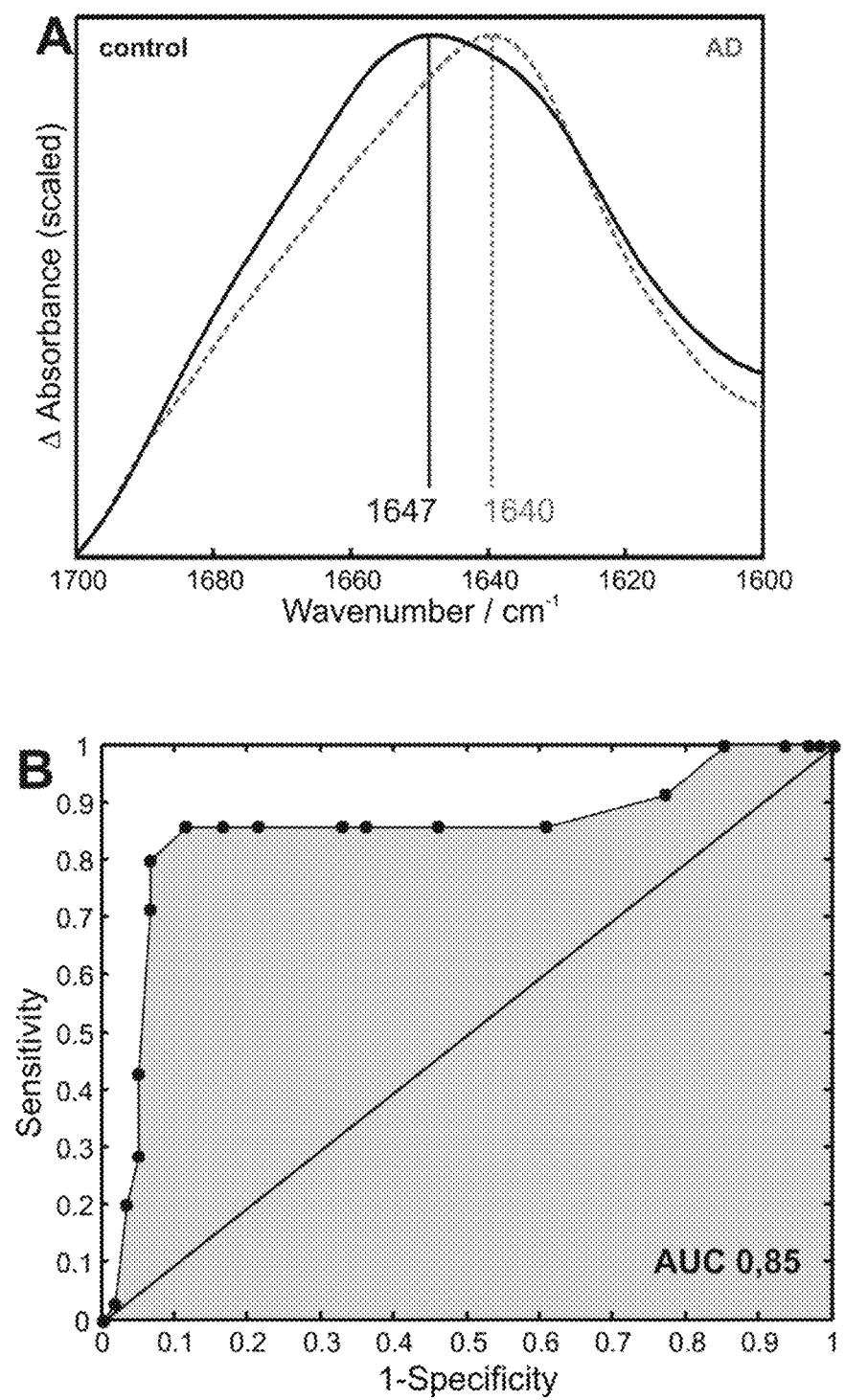
FIG. 10: The average amide I bands of 35 AD and 61 non-neurodegenerative control patients as detected from blood plasma (A) indicate a similar frequency downshift in AD patient samples as detected in CSF. Using a frequency threshold as discriminator, the ROC curve indicated an AUC of 0.85 (B).

Example 8: 1E8 and Antibodies Specific for Oligomers and Fibrils Applied for CSF Analysis The exemplarily demonstrated antibodies 1E8 and A8978 sense both monomerised and fibrillised Aß peptides (FIG. 6A). For diagnostic purposes, the enhanced specificity of A8978 antibody sensing a central Aß epitope proved advantageous over the 1E8 antibody, when a complex body fluid was analysed. 1E8 is known to cross-react with sAPPalpha (N-terminal fragment of amyloid precursor protein (APP) after alpha-secretase processing) due to its N-terminal Aß epitope. A disease-related conformation of sAPPalpha has not been reported, and the overlaying signal hinders a clear-cut sensor readout (FIG. 16A). For a stringent separation of AD from control Aß peptide conformations, the enhanced specificity of a central epitope antibody as A8978 is required (FIGS. 9, 10 and 11).

Using conformation-specific antibodies against oligomers (FIG. 16B) or fibrils (FIG. 16C) did not exhibit disease specific sample features. Both conformations were present in AD and control patient CSF samples. Therefore, the intended diagnostic system has to be prepared with antibodies that are unspecific for the epitope's conformation.

Example 9: Application of the Sensor for Alpha-Synuclein Analysis as Present in Blood Serum with Regard to Parkinson's Disease (PD)

Figure 17:
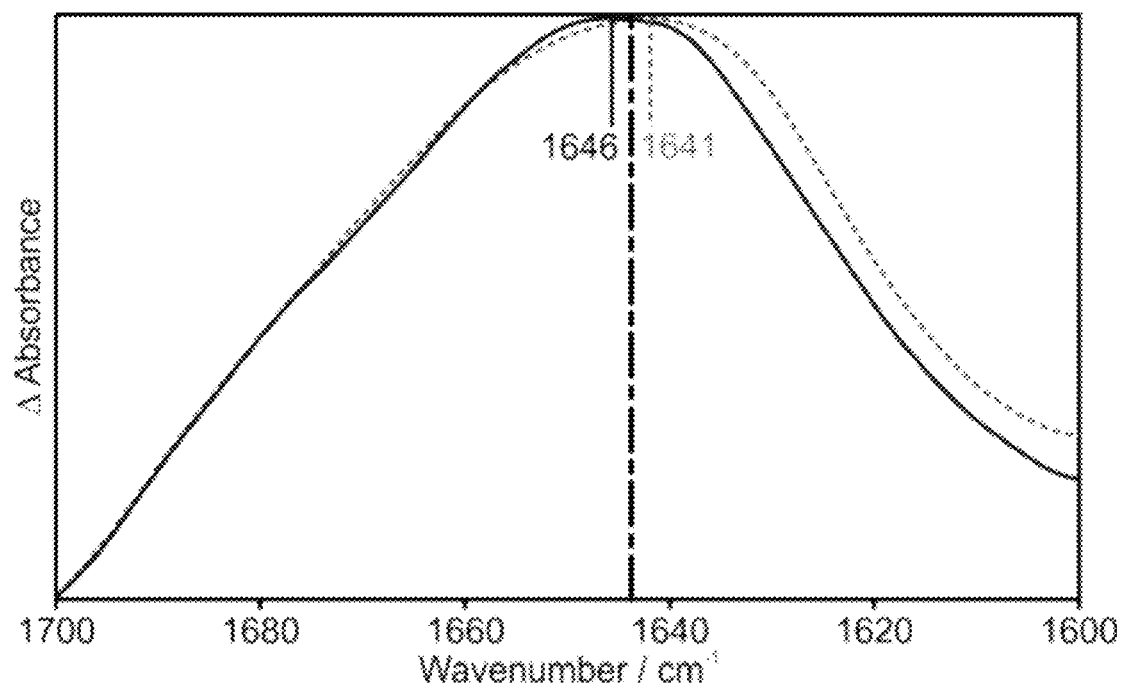
FIG. 17: The blood serum-borne alpha-synuclein fraction as captured with antibody 4B12 exhibited a similar conformational transition in blood samples of control (black, solid) and PD patients (grey, dashed line) dividable by a threshold (dash-dotted line).

The sensor element was typically prepared, polished and silanized. For alpha-synuclein specific functionalization, 4B12 monoclonal antibody (Covance, BioLegend Inc.) was immobilized on the sensor, followed by casein blocking. The recorded spectra of alpha-synuclein as present in blood serum exhibited a clearly downshifted amide I band maximum frequency at 1641 cm$^{-1}$ in the PD sample as compared to 1646 cm$^{-1}$ recorded of the control patient sample. Thereby, the applicability of the sensor for label-free PD diagnostics on blood samples is shown (FIG. 17).

What is claimed is:

1. A method for determining in a body fluid an average secondary structure composition of a protein undergoing conformational transitions associated with disease progression, comprising the steps of:
   (a) conducting, in an infrared (IR) cell comprising an IR sensor element having a functionalized surface with at least one receptor grafted onto said functionalized surface and capable of specific and conformationally independent binding to the protein, a flux of body fluid comprising the protein but not pretreated to isolate or concentrate the protein, wherein the IR sensor element is configured to detect different conformations of the secondary structure of the protein in the body fluid;
   (b) submitting an IR beam through said cell and obtaining an IR spectrum therefrom; and
   (c) detecting an amide I band maximum of the protein to determine the average secondary structure composition of the protein present in the body fluid.

2. The method of claim 1, wherein the IR sensor element comprises a germanium internal reflection element having a trapezoid or parallelogram shape and being transparent in the IR band with sufficient signal to noise ratio to detect the amide I band, the at least one receptor for the biomarker protein capable of specific and conformationally independent binding to the candidate biomarker protein and being directly grafted to at least one surface of said internal germanium reflection element by silanization with short silane linkers or by thiolation with short thiol linkers, reacting freely accessible amine groups of said at least one receptor with amine-reactive groups on the short silane/thiol linkers, and blocking remaining amine-reactive groups on the short silane/thiol linkers with a blocking substance not cross-reacting with the candidate biomarker protein, wherein the short silane linkers and short thiol linkers have a chain length of not more than 20 atoms.

3. The method of claim 1, wherein the receptor is an antibody.

4. The method of claim 3, wherein:
   (i) the candidate biomarker protein is amyloid-beta peptide and the antibody is an antibody specifically binding to the central epitope of the amyloid beta peptide; or
   (ii) the candidate biomarker protein is alpha synuclein and the antibody is an antibody specifically binding to the central epitope of the alpha synuclein peptide without conformational specificity.

5. The method of claim 4, wherein the candidate biomarker is amyloid-beta peptide and the antibody is A 8978.

6. The method of claim 4, wherein the candidate biomarker protein is alpha synuclein and the antibody is 4B12 or S5566.

7. The method of claim 1, wherein the method further comprises one or more of the following steps:
(i) prior to step (a): installing the IR sensor element in an IR cell;
(ii) step (d): analyzing the obtained IR spectrum to classify the sample with statistical methods based on the secondary structure composition of the candidate biomarker protein; and/or
(iii) step (e): regenerating the surface of the infrared element by application of a solution of free ligand for the receptor.

8. The method of claim 1, wherein the spectrum obtained in step (b) has a sufficient signal to noise ratio to resolve the amide I band.

9. The method of claim 1, wherein step (c) comprises comparing the obtained IR spectrum with a spectrum of the candidate biomarker protein with known secondary structure and/or with known concentration.

10. The method of claim 1, further comprising,
(i) parallel to the IR analysis, detection by an additional optical method at different wavelengths; and/or
(ii) combining immuno-ATR-IR vibrational spectroscopy with parallel fluorescence spectroscopy.

11. The method of claim 1, wherein the method is suitable for directly determining the candidate biomarker protein in a body fluid selected from cerebrospinal fluid, blood, and serum, without pretreatment.

12. The method of claim 1, wherein the method is suitable for separate in-vitro or online determination of the candidate biomarker protein.

13. The method of claim 1, wherein the candidate biomarker protein is amyloid-beta associated with Alzheimer's disease, wherein a down shift of the amide I band maximum of the amyloid-beta peptide to a frequency below a threshold value of 1638-1648 $cm^{-1}$ is indicative for progression of Alzheimer's disease.

14. The method of claim 1, wherein the candidate biomarker protein is alpha-synuclein associated with Parkinson's disease, wherein a down shift of the amide I band maximum of the alpha-synuclein peptide to a frequency below a threshold value of 1638-1648 $cm^{-1}$ is indicative for the progression of Parkinson's disease.

15. The method of claim 10, wherein the additional optical method comprises UV/Vis fluorescence analysis.

16. The method of claim 1, further comprising determining the quantity of the candidate biomarker protein present in the body fluid of the patient.

\* \* \* \* \*